US007338768B1

(12) United States Patent
Trau et al.

(10) Patent No.: US 7,338,768 B1
(45) Date of Patent: Mar. 4, 2008

(54) CARRIER-REPORTER BEAD ASSEMBLIES

(75) Inventors: Mathias Trau, Queensland (AU); Darryn Edward Bryant, Queensland (AU)

(73) Assignee: Nanomics Biosystems Pty. Ltd., St. Lucia, Queensland (AU)

( * ) Notice: Subject to any disclaimer, the term of this patent is extended or adjusted under 35 U.S.C. 154(b) by 0 days.

(21) Appl. No.: 09/554,376

(22) PCT Filed: Nov. 12, 1998

(86) PCT No.: PCT/AU98/00944

§ 371 (c)(1),
(2), (4) Date: Jan. 4, 2001

(87) PCT Pub. No.: WO99/24458

PCT Pub. Date: May 20, 1999

(30) Foreign Application Priority Data

Nov. 12, 1997 (AU) .................................. PP0328/97

(51) Int. Cl.
*G01N 33/53* (2006.01)
*C40B 70/00* (2006.01)

(52) U.S. Cl. .......................................... 435/7.1; 506/41
(58) Field of Classification Search .................... 435/4, 435/6, DIG. 40, DIG. 41, 7.1, DIG. 22; 436/523–535
See application file for complete search history.

(56) References Cited

U.S. PATENT DOCUMENTS 4,235,716 A * 11/1980 Halpaap et al. ............... 210/31
5,487,973 A * 1/1996 Nilsen et al. .................. 435/6
5,751,629 A * 5/1998 Nova et al. .................. 365/151

FOREIGN PATENT DOCUMENTS

WO    WO 93/06121    4/1993
WO    WO 96/30392    10/1996

OTHER PUBLICATIONS

Webster's II New Riverside Dictionary, 1994, Houghton Mifflin Co., Boston, p. 282.*
Ferenc Sebestyen et al., "Binary Synthesis of Multicomponent Peptide Mixtures by the Portioning-mixing Technique", *Journal of Peptide Science*, vol. 1, 26-30 (1995).
Eugen Campian et al., "Synthesis of Support-Bound Peptides Carrying Color Labels", *Drug Development Research*, 33:98-101 (1994).
W. H. Moos et al., "An integrated approach to exploiting molecular diversity", *Med. Chem.*, pp. 137-142 (1995).

* cited by examiner

*Primary Examiner*—Mark L. Shibuya
(74) *Attorney, Agent, or Firm*—Proskauer Rose LLP

(57) ABSTRACT

An assembly of a carrier having one or more reporter beads non-covalently attached thereto which may be used in relation to oligomer libraries. The oligomer libraries may be formed by a combinatorial split-process-recombine procedure. The oligomer library comprises a plurality of molecules comprising a multiplicity of different chemical groups. Each reporter bead has a different marker associated therewith to identify the chemical group attached to the carrier as well as to identify the position in sequence of the chemical group relative to other chemical groups in each molecule of the library. The markers are selected from fluorophores, chromophores, bar codes or radioactive or luminescent labels.

13 Claims, 18 Drawing Sheets
(8 of 18 Drawing Sheet(s) Filed in Color)

100 μm

100 μm

100 μm 100 micron 100 micron

100 μm 100 micron

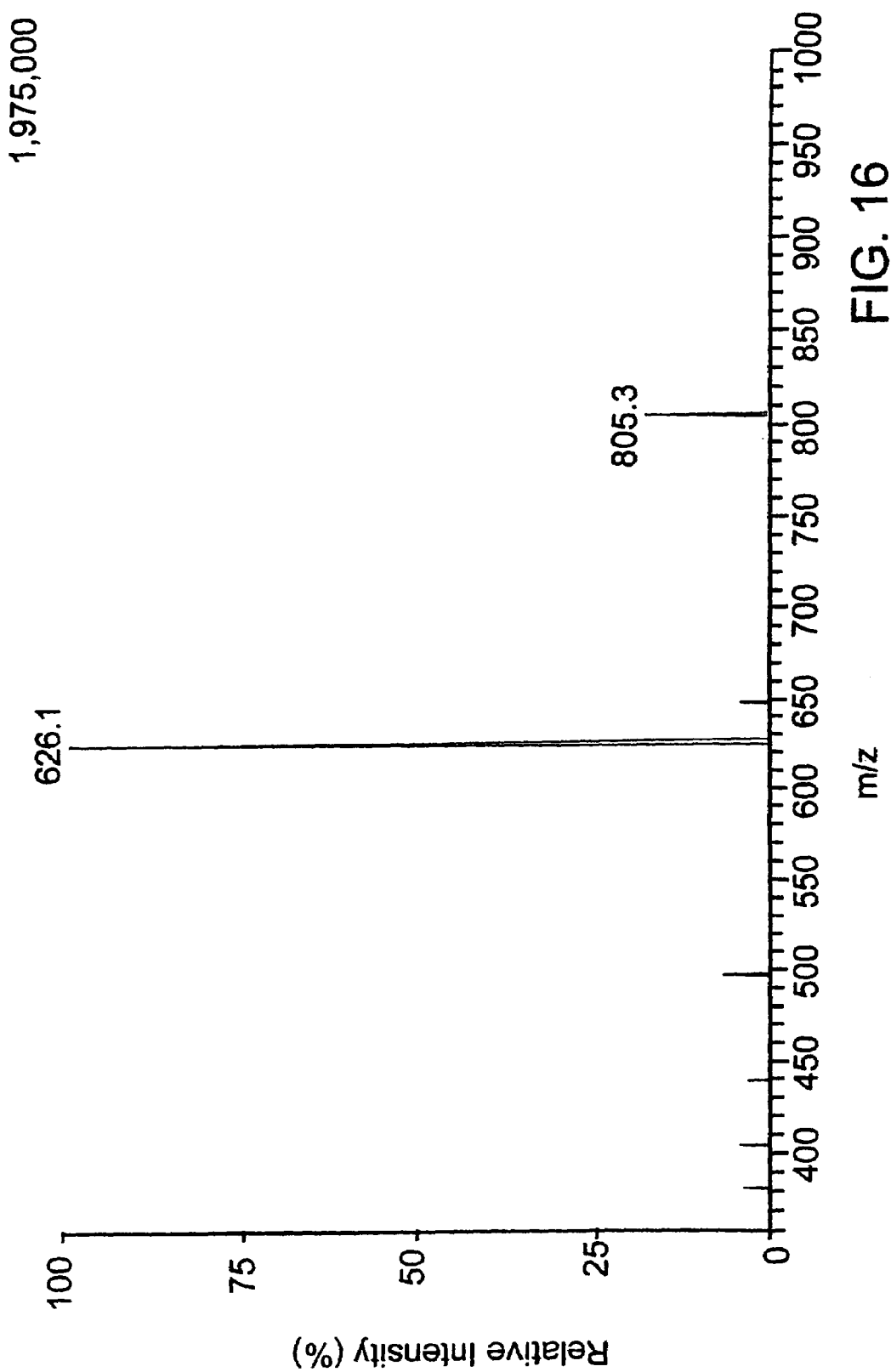

US 7,338,768 B1

CARRIER-REPORTER BEAD ASSEMBLIES

CROSS-REFERENCE TO RELATED APPLICATIONS

This application is the National Phase of International Application No. PCT/AU98/00944, filed Nov. 12, 1998, which claims benefit of Australian Application No. PP 0328, filed Nov. 12, 1997.

FIELD OF THE INVENTION

THIS INVENTION relates generally to carrier-reporter bead assemblies and their use in relation to oligomer libraries which may be formed by a combinatorial split-process-recombine procedure as well as a method for decoding molecules produced in such oligomer libraries.

BACKGROUND OF THE INVENTION

Split-process recombine methods in combinatorial chemistry are already known in relation to formation of peptide libraries as discussed in Gallop et al., 1994, J. Med. Chem. 37 1233-1251 which refers to synthesis of peptide libraries by the use of polystyrene beads which are initially present as a first batch which are split into smaller batches wherein different amino acids are covalently attached to a primary linker group present on the surface of each bead. Subsequently, the beads are recombined and then split again so that a second amino acid may be attached to the amino acid attached to the primary linker group. This process is repeated a number of times as may be required to produce the peptide library.

A similar procedure is described in Gallop et al., 1994, supra which refers to the establishment of an oligonucleotide library.

"Split-process-recombine" or "split synthesis" methods generating one (resin) bead-one compound libraries were first proposed in Furka et al., 1991, Int. J. Pept. Protein Res. 37 487-493 and are also discussed in Eichler et al., 1995, Medicinal Research Reviews 15(6) 481-496 and Balkenhohl et al., 1996, Angew. Chem. Int. Ed. Engl. 35 2288-2337.

Peptide libraries are mainly used in drug discovery as discussed in Gallop et al., 1994, supra wherein potentially useful drugs are identified by screening methods as are known in the art. This is also reported in Borman Chemical & Engineering News, February 1997, 43-62, Fruchtel et al., 1996, Angew. Chem. Int. Ed. Engl. 35 17-42 and Barany et al., 1987, In. J. Peptide Protein Res. 30 705-739.

Oligonucleotide libraries, on the other hand, are useful as a tool for rapid DNA sequencing by hybridization as discussed in Fodor et al., 1991, Science 251 767, Lysov et al., 1988, Dokl. Akad. Nauk. SSSR 303 1508, Bains et al., 1988, J. Theor. Biol. 135 303, Drmanac et al., 1989, Genomics 4 114 and Drmanac et al., 1993, Science 260 1649.

Sequencing by hybridization (SBH) has been proposed to replace conventional DNA sequencing technology which is a laborious procedure involving electrophoretic size separation of labelled DNA fragments. SBH uses a set of short oligonucleotide probes of defined sequence to search for complementary sequences on a longer target strand of DNA. The hybridization pattern is used to reconstruct the target DNA sequence.

The challenge with implementing SBH techniques as a viable method of sequencing of DNA is that an extremely large number of probes is required. New methods have been proposed to overcome this problem as discussed in Fodor et. al., 1991, supra, Pease et al., 1994, Proc. Natl. Acad. Sci. 91 5022, Cho et al., 1993, Science 261 1303 and Southern et al., 1992, Genomics 13 1008. These new methods involve the use of oligonucleotide arrays or "biological chips" as discussed in Fodor et al., 1991, supra, which harbour specified chemical compounds (i.e. the probes) at precise locations in an array format. The target DNA is then added to the array of probes. The hybridization pattern, determined in a single experiment, directly reveals the identity of all complementary probes as reported in Drmanac et al., 1989, supra and Drmanac et al., 1993, supra. Although this technique holds much promise, the information density on each array is extremely low for the purpose of DNA sequencing and this limits the size and speed with which DNA fragments can be sequenced. The difficulties associated with selectively anchoring oligonucleotide sequences to specific and spatially arranged sites on the substrate means that the minimum pixel size in the arrays is limited currently to approximately 0.4 mm×0.4 mm in area. As pixel size directly determines information density and hence sequencing efficiency, miniaturization of the "biological chips" is a major technical problem for implementing this technology as a rapid method of sequencing. One method of overcoming this problem is the use of a technique requiring "field induced colloidal crystallization" as reported in Trau et al., 1996, Science 272 706. This technique uses miniaturized chips of patterned microscopic colloidal particles which contain chemisorbed oligonucleotides on a transparent electrode comprising indium tin oxide. Fluorescent hybridization patterns of unknown DNA sequences with the arrays are observed using an optical microscope.

Before the advent of the technique of Trau et al., 1996, supra, SBH was previously carried out by attaching target DNA to a surface and sequentially interrogating with a set of oligonucleotide probes, one at a time as discussed in Drmanac et al., 1989, supra, Drmanac et al., 1993, supra and Strezoska et al., 1991, Proc. Nat. Acad. Sci. USA 88 10089 which was time consuming and inefficient.

Application of conventional split-process-recombine methods to drug discovery and SBH is, however, currently limited by the inherent difficulty of rapidly, and conveniently, identifying the unique sequence of events applicable to any chosen multimeric molecule. For large numbers of carriers and large numbers of steps and/or processing methods, this "identification" procedure is particularly difficult. In many practical cases, where high throughput and fast analysis is required, this problem is intractable by conventional methods.

The conventional split-process-recombine technologies referred to above presented difficulties when it was desired to detect and isolate a molecule of interest. In this regard, it was necessary to detect the molecule of interest by use of a suitable assay or probe and then isolate the molecule of interest by cleaving that molecule from the bead and subsequently identifying the molecule by techniques such as mass spectroscopy or HPLC. This was time consuming and cumbersome and in some cases, cleavage was not possible.

Reference may be made to International Publication WO93/06121 which refers to a general stochastic method for synthesizing libraries of random oligomers, which are synthesized on solid supports inclusive of polystyrene beads or which may be cleaved from these supports to provide a soluble library. The oligomers are composed of a sequence of monomers that can be joined together to form an oligomer or polymer. This reference also describes the use of identifier tags to identify the sequence of monomers in the oligomer. The identifier tag may be attached directly to the oligomer with or without an accompanying particle, to a linker attached to the oligomer, to the solid phase support on which the oligomer is synthesized or to a second particle attached to the oligomer carrying particle. However, the only means of attachment described in this reference is by way of covalent bonding. In this reference, the identifier tag is described in very broad terms, such as any recognizable feature, which includes a microscopically distinguishable shape, size, colour or optical density; a differential absorbance or emission of light; chemical reactivity; magnetic or electronic coiled information; or any other distinctive mark with the required information and decipherable at the level of one or a few solid supports. In one form, the identifier tags are described as small beads of recognizably different shapes, sizes or colours or labelled with bar codes.

However, while the description of International Publication WO93/06121 refers very broadly to the types of identifier tags that may be utilized in the method of formation of oligomer libraries, the only experimental evidence referred to in the specification is the use of oligonucleotides. Thus, there is no enabling disclosure especially in relation to the use of small beads as identifier tags and how this particular technique may be put into practical effect.

In International Publication WO93/06121, reference is made to identifying the tags by sequencing or hybridization if the tag is an oligonucleotide. One can also amplify the oligonucleotide tag by PCR. However, it will be appreciated that such identification methods are time consuming and inefficient. For example, use of PCR may result in PCR product contamination making it necessary to introduce further measures to overcome this problem as described in International Publication No. WO93/06121. It is also necessary to sequence amplified DNA and this involves an additional step in the identification procedure as described in International Publication No. WO93/06121.

Reference may also be made to U.S. Pat. No. 5,721,099 which describes complex combinatorial chemical libraries of compounds encoded with tags. Each compound in the library is produced by a single reaction series and is bound to an individual solid support which may include particles or beads inclusive of polystyrene beads or silica gel beads. Each solid support has bound to it a combination of four distinguishable identifiers which differ from one another. The combination provides a specific formula comprising a tag component capable of analysis and a linking component capable of being selectively cleaved to release the tag component. Each identifier or combination thereof encodes information at a particular stage in the reaction series for the compound bound to the solid support. However, it is essential in this library that prior to analysis, each tag component must be cleaved from the support thus creating at least one additional step which is time consuming and inefficient and thus the same disadvantages relevant to International Publication WO93/06121 also apply in the case of this reference.

In relation to using single stranded identifier tags to encode combinatorial peptide synthesis, which method is discussed in Needles et al., 1993, Proc. Natl. Acad. Sci. U.S.A. 90 10700-10704, such method was disadvantageous because of the reasons discussed above in International Publication WO93/06121. However, it is also noted that after detection of a peptide or molecule within the library of interest, in some cases it was necessary to cleave the corresponding tag from the support and amplify the tag by PCR because it was only present in trace amounts. This was also time consuming and inefficient.

Reference may also be made to photolabile or electrophoretic tagging as described in Ohlmeyer et al., 1993, Proc. Nat. Acad. Sci. USA 90 10922-10926 or Gallop et al., 1994, supra which was also disadvantageous because of the inclusion of additional steps prior to identification of the tag.

OBJECT OF THE INVENTION

It is therefore an object of the present invention to provide an assembly of a carrier and one or more reporter beads which assembly may be used to form a synthetic oligomer library suitably, although not exclusively, by a combinatorial split-process-recombine procedure.

Another object of the invention is to provide an oligomer library wherein a molecule of interest in the library may be directly identified or decoded without the requirement of any preliminary step as was the case in the prior art.

SUMMARY OF THE INVENTION

According to one aspect of the invention, there is provided an assembly of a carrier having one or more reporter beads non-covalently attached thereto.

Such an assembly may be used in many applications, such as combinatorial chemistry procedures which do not involve a split-process-recombine procedure. Preferably, however, such assemblies are used in combinatorial chemistries which do involve a split-process-recombine procedure.

According to another aspect of the invention, there is provided a method of forming the above assembly including the step of non-covalently attaching one or more reporter beads to a carrier.

According to yet another aspect of the invention, there is provided a method for forming a synthetic oligomer library comprising a plurality of molecules comprising a multiplicity of different chemical groups, said method including the steps of:—

(i) attaching a respective chemical group to a carrier in each of a plurality of reaction vessels;

(ii) attaching a reporter bead to the carrier in non-covalent manner in each reaction vessel wherein each reporter bead has a marker associated therewith;

(iii) combining the carriers from each reaction vessel resulting from steps (i) and (ii) into a recombination vessel;

(iv) splitting the carriers from the recombination vessel into the plurality of reaction vessels wherein steps (i) and (ii) are repeated; and (v) repeating steps (iii) and (iv) until the library of molecules is formed wherein each molecule will have a unique signal associated therewith which signal is dependent on different combinations of markers to facilitate direct identification of the sequence of chemical groups comprising said molecule;

wherein step (ii) can be carried out prior to or simultaneously with step (i).

It will be appreciated having regard to the above that the term "chemical group" refers to the chemical units or entities that are added one at a time in regard to the synthesis of the molecule. For example, in relation to the formation of an oligopeptide or polypeptide, it is the individual amino acids that comprise the chemical groups. In another example, in relation to the synthesis of an oligonucleotide, it is the basic nucleotides or building blocks of the oligonucleotide that comprise the chemical groups.

The invention in further aspect refers to an oligomer library comprising a plurality of different molecules having a multiplicity of different chemical groups which has been formed by the aforementioned method.

The invention in yet a further aspect refers to an oligomer library comprising a plurality of different molecules wherein each molecule is attached to a respective carrier and wherein there is also provided a plurality of reporter beads attached to the carrier and/or to adjacent reporter beads in non-covalent manner characterized in that each reporter bead has a marker associated therewith to identify the chemical group attached to the carrier as well as to identify the position in sequence of the chemical group relative to other chemical groups in each molecule whereby each molecule in the library will have a unique signal associated therewith which signal is dependent on different combinations of markers to facilitate direct identification of each molecule.

The use of the term "direct" in this context means that each molecule can be identified without the necessity of any preliminary step inclusive of cleaving of the molecule from the carrier and amplification by PCR or by use of hybridization or sequencing as was the case with the prior art, particularly International Publication WO93/06121.

The advantage of direct identification of each molecule means that such molecule can then be synthesized in conventional manner once the unique combination of chemical groups associated with each molecule is known.

In regard to the prior art, it will be appreciated that efficient direct identification or decoding of a molecule of interest could not occur because molecular tags which were covalently bonded to the carrier were not usually detectable unless they were cleaved from the carrier or amplified in the case of nucleic acids. The use of molecular tags also severely limits the maximum possible size of chemical libraries which can be encoded. Although reference was made in the prior art that small reporter beads could be attached to larger carrier beads, this was not enabled, and apart from covalent attachment, no method of achieving this outcome was suggested. In reality, permanent attachment of reporter beads to carriers could not be achieved unless non-covalent forces were taken into consideration, as is the case of the present invention.

It has now been ascertained in accordance with the present invention that by attaching a reporter bead to a carrier in a non-covalent manner that efficient attachment or adherence of the reporter bead to the carrier may be achieved so as to facilitate direct identification or decoding of a molecule of interest within the oligomer library. One example of non-covalent attachment is the use of electrostatic forces wherein surface charges may be induced on either the carrier, reporter bead or both.

However, for the sake of convenience, it has been elucidated by the inventors that use of colloidal particles as reporter beads greatly facilitates non-covalent attachment of the reporter beads to the carrier. A suitable definition of colloidal particles is referred to in Hunter (R. J. Hunter, 1986, "Foundations of Colloid Science", Oxford University Press, Melbourne, which is incorporated herein by reference).

Thus, when one substance dissolves in another to form a true solution, the ultimate particles of the solute are of molecular dimensions. The radius of the solute molecule in these cases is seldom more than a nanometer and usually less. Solvent and solute molecules are of comparable size and the solute molecules are usually dispersed uniformly through the (continuous) solvent. There is an important class of materials, however, in which the units that are dispersed through the solvent are very much larger in size than the molecules of the solvent. Such systems are called colloidal dispersions. The large particles present in such systems are referred to as colloids.

The size of such colloids varies greatly (depending on the system under study). Typically, a colloidal particle is defined as any particle (i.e., piece of matter) which possesses one microscopic size dimension (i.e., one dimension smaller than that visible by the naked eye). A feature of colloidal systems is that the area of contact between the disperse particles and the dispersion medium, or between more than one dispersed particle, is relatively large.

Because of their macroscopic nature, colloidal particles exhibit interaction forces which are quite different to those of molecular systems. By colloidal forces, we refer to the standard definition used in text books such as Hunter, 1986, supra or Russel et al., 1989, "Colloidal Dispersions", Cambridge University Press, Cambridge, which is also incorporated herein by reference.

As such particles approach each other, or as they approach some other surface, they will be subject to a variety of macroscopic (i.e., non-covalent) physical forces. Examples of such forces, although by no means an exhaustive list, include:—
(i) van der Waals forces (attractive forces resulting from an intrinsic van der Waals interaction between colloids);
(ii) electrostatic forces (attractive or repulsive interaction resulting from surface charge on the colloidal particles);
(iii) steric forces (attractive or repulsive interaction resulting from a surface coating of polymers); and
(iv) bridging flocculation (attractive forces resulting from the interchange of adsorbed polymer strands from one colloid to another).

It will also be appreciated that non-covalent attachment of reporter beads to carriers has significant advantages when compared to covalent attachment of reporter beads and molecular tags to carriers. Thus, non-covalent attachment of reporter beads to carriers works because of the harnessing of colloidal forces. Covalent attachment without optimisation of the colloidal forces involved of reporters to carriers may not survive the processes associated with combinatorial synthesis. Reporters as small beads need to be sufficiently large to contain enough fluorophores (for example) to be detected easily (i.e., at least 500 fluorophore molecules per bead). This means the beads need to be much larger than a molecule which undergoes a covalent bond. If the small beads were covalently attached to a carrier, then there would be only a few bonds holding a relatively larger reporter. The small beads would be detached very quickly by abrasion against other carriers if there were no colloidal (i.e. non-covalent) forces involved.

The non-covalent attachment does not interfere with the chemical synthesis apart from occupying a portion of available surface area. Covalent attachment of tags, as was the case with the prior art discussed above, means performing extra chemical steps at each stage of the chemical process.

The non-covalent attachment of small beads to the carrier can be performed relatively easily by mixing carriers with reporters in a solvent. The use of non-covalently attached reporters means that there are no artifacts being produced within the tags or ligands by interaction between them. Also, the small reporter beads do not require cleaving and chemical analysis for decoding. This saves time and money.

The invention also has a capacity to determine the sequence of reaction steps when larger numbers of processes or steps are involved as described in detail hereinafter.

It will also be appreciated that the number of markers which can be used is relatively small and, in most cases, can be equal to nine or less as will also be apparent from the following description.

The term "oligomer" as used herein has the same meaning as discussed in International Publication WO93/06121 which is herein incorporated by reference and thus may comprise a sequence of monomers which are any member of a set of molecules that can be joined together to form an oligomer or polymer, i.e., amino acids, carbonates, sulfones, sulfoxides, nucleosides, carbohydrates, ureas, phosphonates, lipids, esters or combinations thereof.

The term "oligomer" as used herein also includes within its scope a plurality of inorganic units attached to each other in a particular sequence. Examples of inorganic units are silicates and aluminosilicates.

The invention in another aspect also includes a process of decoding molecules which are encoded by the process of the invention which includes the step of analysis of the reporter beads as described hereinafter so as to determine the unique sequence of the chemical groups which comprise each of the molecules.

It therefore will be appreciated that, in another aspect of the invention, there is provided a process for identification of a particular molecule having a certain unique sequence by the decoding process described above.

It will also be appreciated that while the preferred embodiment described hereinafter refers to the formation of oligonucleotides or oligopeptides wherein nucleotides or amino acids correspond to the chemical groups as discussed above, the process of the invention is applicable to the formation of oligomers or polymers from identical monomer units or formation of relatively complex molecules or macromolecules from individual or different chemical groups or components as will be apparent from the meaning of "oligomer" discussed above.

In particular, the process of the invention is applicable to any type of chemical reaction that can be carried out on a solid support and thus includes, for example:—

(i) [2+2] cycloadditions including trapping of butadiene;
(ii) [2+3] cycloadditions including synthesis of isoxazolines, furans and modified peptides;
(iii) acetal formation including immobilization of diols, aldehydes and ketones;
(iv) aldol condensation including derivatization of aldehydes, synthesis of propanediols;
(v) benzoin condensation including derivatization of aldehydes;
(vi) cyclocondensations including benzodiazepines and hydantoins, thiazolidines, β-turn mimetics, porphyrins, phthalocyanines;
(vii) Dieckmann cyclization including cyclization of diesters;
(viii) Diels-Alder reaction including derivatization of acrylic acid;
(ix) electrophilic addition including addition of alcohols to alkenes;
(x) Grignard reaction including derivatization of aldehydes;
(xi) Heck reaction including synthesis of disubstituted alkenes;
(xii) Henry reaction including synthesis of nitrile oxides in situ (see [2+3]cycloaddition);
(xiii) catalytic hydrogenation including synthesis of pheromones and peptides (hydrogenation of alkenes);
(xiv) Michael reaction including synthesis of sulfanyl ketones, bicyclo]2.2.2]octanes;
(xv) Mitsunobu reaction including synthesis of aryl ethers, peptidyl phosphonates and thioethers;
(xvi) nucleophilic aromatic substitutions including synthesis of quinolones;
(xvii) oxidation including synthesis of aldehydes and ketones;
(xviii) Pausen-Khand cycloaddition including cyclization of norbornadiene with pentynol;
(xix) photochemical cyclization including synthesis of helicenes;
(xx) reactions with organo-metallic compounds including derivatization of aldehydes and acyl chlorides;
(xxi) reduction with complex hydrides and Sn compounds including reduction of carbonyl, carboxylic acids, esters and nitro groups;
(xxii) Soai reaction including reduction of carboxyl groups;
(xxiii) Stille reactions including synthesis of biphenyl derivatives;
(xxiv) Stork reaction including synthesis of substituted cyclohexanones;
(xxv) reductive amination including synthesis of quinolones;
(xxvi) Suzuki reaction including synthesis of phenylacetic acid derivatives; and
(xxvii) Wittig, Wittig-Horner reaction including reactions of aldehydes; pheromones and sulfanyl ketones.

Reference may also be made to Patel et al., April 1996, DDT 1(4) 134-144 which refers to manufacture or synthesis of N-substituted glycines, polycarbamates, mercaptoacylprolines, diketopiperazines, HIV protease inhibitors, 1-3 diols, hydroxystilbenes, B-lactams, 1,4-benzodiazepine-2-5-diones, dihydropyridines and dihydropyrimidines.

Reference may also be made to synthesis of polyketides as discussed in Rohr, 1995, Angew. Int. Ed. Engl. 34 881-884.

The carriers for use in the method of the invention are suitably polymeric supports such as polymeric beads which are preferably formed from polystyrene crosslinked with 1-5% divinylbenzene. Carrier beads may also be formed from hexamethylenediamine-polyacryl resins and related polymers, poly[N-{2-(4-hydroxylphenyl)ethyl}] acrylamide (i.e. (ONE Q)), silica, cellulose beads, polystyrene beads, latex beads, grafted copolymer beads such as polyethylene glycol/polystyrene, pore-glass beads, polyacrylamide beads, dimethylacrylamide beads optionally cross-linked with N,N'-bis-acrylolyl ethylene diamine, glass particles coated with a hydrophobic polymer inclusive of cross-linked polystyrene or a fluorinated ethylene polymer which provides a material having a rigid or semi-rigid surface, poly(N-acryloylpyrrolidine) resins, p-benzyloxybenzyl alcohol resin (WANG resin), 4-hydroxymethylphenylacetamidomethyl resin (PAM resin), chloromethylpolystyrene-divinylbenzene resin (MERRIFIELD resin), polyethylene glycol/polystyrene resin (PAP resin), polyamide resin, polyethylene functionalized with acrylic acid, kieselguhr/polyamide (Pepsyn K), polyacrylamide/polystyrene copolymer (POLYHIPE), polystyrene/polydimethylacrylamide copolymers, controlled pore glass (CPG), polystyrene macrobeads, polystyrene/polyethylene glycol (TENTAGEL) and polyethylene glycol-polystyrene/divinylbenzene copolymers.

These carrier materials will usually contain functionalities or be able to be functionalized for attachment of reporter beads or linkers. Suitable functionalities include —$NH_2$, —COOH, —SOH, —SSH or sulfate groups.

It will also be appreciated that the polymeric beads may be replaced by other suitable supports such as pins or chips as is known in the art, e.g. as discussed in Gordon et al., 1994, J. Med. Chem. 37(10)1385-1401. The beads may also be replaced by pellets, discs, capillaries, hollow fibres or needles as is known in the art.

Thus, it can be appreciated from the foregoing that the carrier may comprise any solid material capable of providing a base for combinational synthesis.

Reference is also made to International Publication WO93/06121, which is incorporated herein by reference, which describes a full range of supports that may constitute carriers for use in the method of the invention which may have any suitable shape and be formed from appropriate materials inclusive of latex, glass, gold or other colloidal metal particles and the like.

Reference may also be made to International Publication WO95/25737 or WO97/15390 which are herein incorporated by reference to examples of suitable carriers.

Linkers for use with the supports of the inventions may be selected from base stable anchor groups as described in Table 2 of Fruchtel et al., 1996, supra or acid stable anchor groups as described in Table 3 of Fruchtel et al., 1996, supra. In this regard, the Fruchtel et al., 1996, reference is incorporated herein by reference.

Linkers for use in the method of the invention are also referred to in International Publication WO93/06121.

Generally the anchors developed for peptide chemistry are stable to either bases or weak acids but for the most part, they are suitable only for the immobilization of carboxylic acids.

However, for the reversible attachment of special functional groups, known anchors have to be derivatized and optimized or, when necessary, completely new anchors must be developed. For example, an anchor group for immobilization of alcohols is (6 hydroxymethyl)-3,4 dihydro-2H-pyran, whereby the sodium salt is covalently bonded to chloromethylated Merrifield resin by a nucleophilic substitution reaction. The alcohol is coupled to the support by electrophilic addition in the presence of pyridinium toluene-4 sulphonate (PPTS) in dichloromethane. The resulting tetrahydropyranyl ether is stable to base but can be cleaved by transetherification with 95% trifluoroacetic acid.

Benzyl halides may be coupled to a photolabile α-sulphanyl-substituted phenyl ketone anchor.

It will also be appreciated that the markers for use in the method of the invention include, but not necessarily limited to, fluorophores, chromophores, bar codes or radioactive or luminescent labels as discussed in International Publication WO93/06121. The markers may also include detectable physical features of the beads such as the size of the beads. Preferably, the markers comprise fluorescent dyes. Any suitable fluorescent dye may be used for incorporation into the reporter beads of the invention. For example, reference may be made to U.S. Pat. Nos. 5,573,909 (Singer et al., which is incorporated herein by reference) and 5,326,692 (Brinkley et al., which is incorporated herein by reference) which describe a plethora of fluorescent dyes which may be used in accordance with the present invention.

Reference may also be made to fluorescent dyes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218 which are all incorporated herein by reference.

One or more of the fluorescent dyes are preferably incorporated into a reporter bead, such as a polymeric or ceramic microparticle. The polymeric microparticle can be prepared from a variety of polymerizable monomers, including styrenes, acrylates and unsaturated chlorides, esters, acetates, amides and alcohols, including but not limited to, polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidenechloride and polydivinylbenzene. The microparticles may be prepared from styrene monomers. Ceramic microparticles may be comprised of silica, alumina, titania or any other suitable transparent material.

A suitable method of making silica microparticles is described, for example in "The Colloid Chemistry of Silica and Silicates" Cornell University Press by Ralph Keller 1955.

The microparticles may be of any suitable size or shape. For example, the microparticles may be spherical or irregular in shape. Typically, microparticles which may be used in the present invention have a diameter of about 0.01 µm to about 50 µm.

Fluorescent dyes may be incorporated into microparticles by any suitable method known in the art, such as copolymerization of a polymerizable monomer and a dye-containing comonomer or addition of a suitable dye derivative in a suitable organic solvent to an aqueous suspension as, for example, disclosed in Singer et at., supra including references cited therein. Alternatively, fluorescent microparticles may be produced having at least one fluorescent spherical zone. Such microparticles may be prepared as for example described in U.S. Pat. No. 5,786,219 (Zhang et al.) which is incorporated herein by reference.

It will also be appreciated that one may detect or identify a compound of interest in a compound library of the invention having a unique sequence by a number of screening methods well known in the art without the need for cleaving the molecule of interest from the carrier. When the unique sequence has been determined, a molecule comprising such sequence can by synthesized by conventional means such as amino acid synthesizers or oligonucleotide synthesizers as is known in the art.

One may also apply the method of the invention to SBH technology whereby a library is formed of carrier beads, each of which has attached thereto a unique polynucleotide or oligonucleotide sequence and reporter beads identifying the unique sequence. An aqueous solution of fluorescently labelled ssDNA of unknown sequence may be passed over the library of polynucleotide or oligonucleotide compounds and adsorption (hybridization) of the ssDNA will occur only on carrier beads which contain polynucleotide or oligonucleotide sequences complementary to those on the ssDNA. These carrier beads may be identified, for example, by fluorescence optical microscopy.

Ligands that may be screened in accordance with the invention include agonist and antagonists for cell membrane receptors, toxins, venoms, viral epitopes, hormones, sugars, cofactors, peptides, enzyme substrates drugs inclusive of opiates and steroids, proteins including antibodies, monoclonal antibodies, antisera reactive with specific antigenic determinants, nucleic acids, lectins, polysaccharides, cellular membranes and organibles.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

Reference to a preferred embodiment of the invention is made in the attached drawings, wherein:—

FIG. 16 is a mass spectrograph of a peptide cleaved off the tagged carriers as described in Procedure J in Example 4. The largest peak is at 626.1 which corresponds to the molecular weight of Fmoc-Alanine-Glycine-Lysine-Glycine-OH (SEQ ID NO:1). This is the exact peptide sequence which was synthesized on the carriers in this three-step amino acid coupling and tagging example.

DESCRIPTION OF PREFERRED EMBODIMENT

A split-process-recombine procedure involving n processes and m steps may be defined as follows. Let the n processes be $P_1, P_2, \ldots, P_n$. The event of performing process $P_j$ at the ith step will be denoted by $P_j(i)$. At each stage $i=1, 2, \ldots, m$:

the carriers are partitioned into n subsets $S_1, S_2, \ldots, S_n$;
for $j=1, 2, \ldots, n$ process $P_j$ is performed on the carriers in subset $S_j$;
the carriers are recombined.

Figure 1:
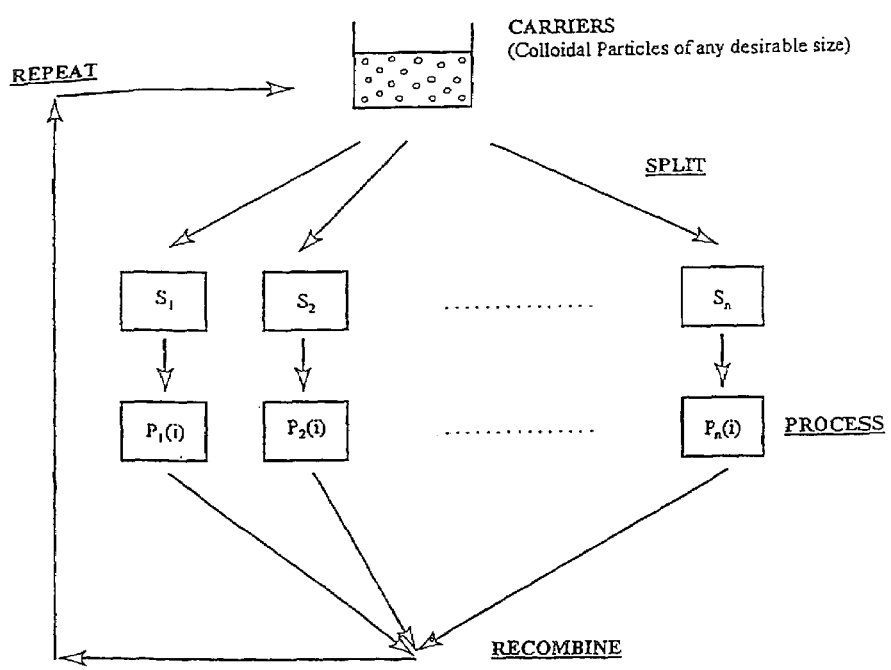
FIG. 1 is a schematic representation of one step in a split-process-recombine procedure, e.g. as discussed in the prior art in relation to the synthesis of peptide libraries.
Figure 2:
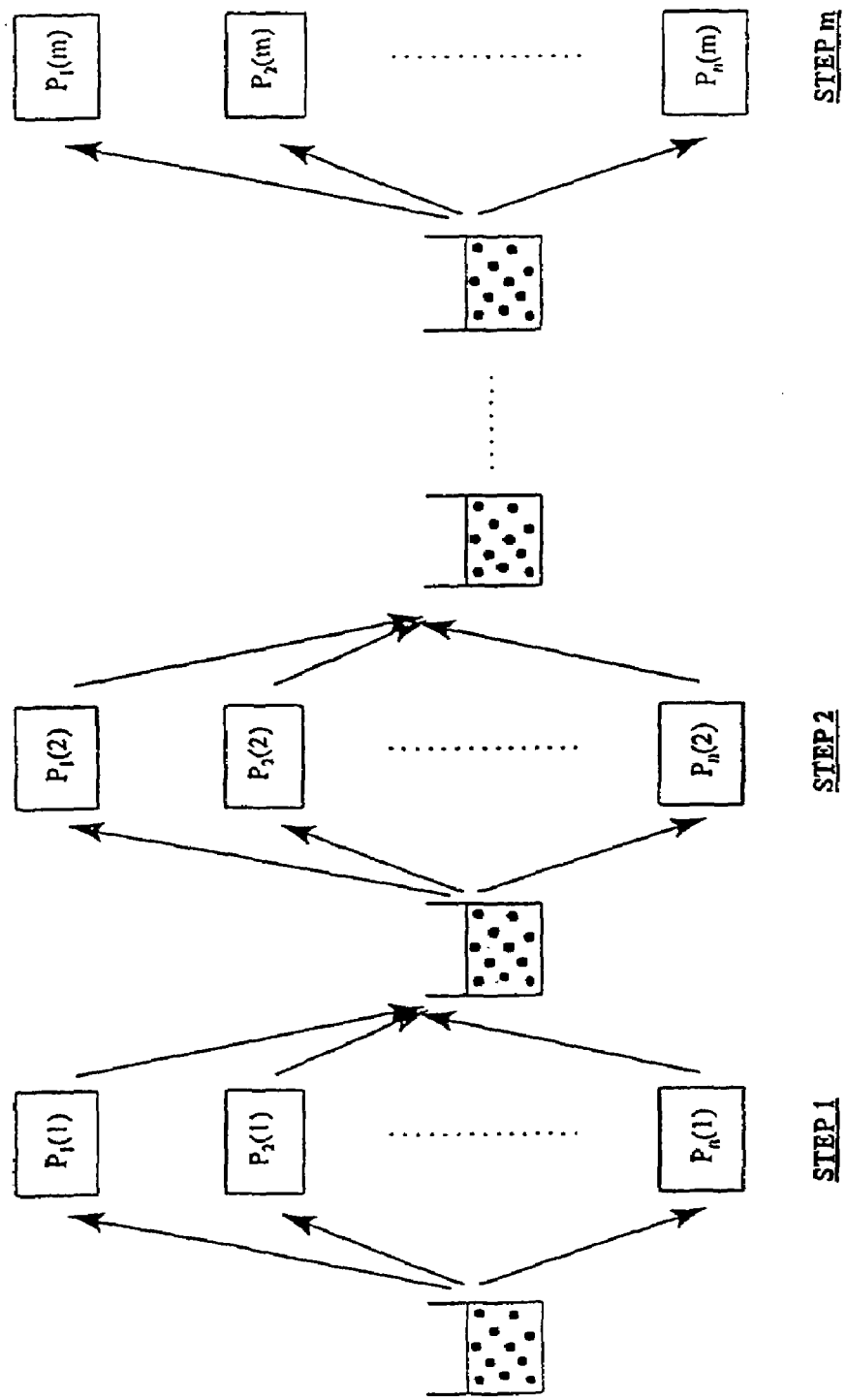
FIG. 2 is a schematic representation of the entire iterative split-process-recombine procedure referred to in FIG. 1.

A schematic representation of this procedure is shown in FIGS. 1 and 2.

Examples of such processes include the combinatorial synthesis of oligonucleotide and oligopeptide chains. In these examples, insoluble polymer beads (colloidal particles, typically 1-1000 μm in diameter) may be used as the carriers onto which nucleic or amino acid monomers are attached and sequentially grown. By performing the split-process-recombine procedure repeatedly for a large number of carriers, a large variety of randomly generated oligonucleotide or oligopeptide sequences can be synthesized. Each carrier thus contains an attached polymer with a unique sequence which is defined by the sequence of processing events which the carrier has experienced (i.e., the specific path which the carrier has followed in FIG. 2).

The present invention relates to a novel and convenient method to determine the sequence of processes applied to a particular carrier involved in a split-process-recombine procedure. This procedure does not involve the chemical tagging of the carrier and by contrast involves the tagging of carriers by non-covalent attachment of reporter beads. This method has several significant advantages over conventional tagging methods:—

(1) Attachment of beads to the carrier can be achieved by simple (physical) processes which do not necessarily involve chemical reactions. Consequently it is extremely unlikely that the tagging procedure will interfere with the reaction processes under study.

(2) The reporter beads may be doped (i.e., imbibed) with a wide variety, and high concentration, of reporter molecules (e.g., fluorescence dyes) to enable facile detection and multi-step tagging without the necessity of chemical grafting, cleaving, and/or amplification.

(3) The presence of beads attached to the carrier is extremely easy to detect via a number of means (e.g., fluorescence emission, infrared spectroscopy). This allows facile and convenient determination of the processing sequences which a carrier has experienced.

A method by which the sequence of processes applied to a particular carrier involved in a split-process-recombine procedure can be determined at the conclusion is now described.

For $i=1, 2, \ldots, m$ and for $j=1, 2, \ldots, n$ a batch $B_j(i)$ of reporter beads is required. These reporter beads will have the property that the batch to which any particular reporter bead belongs can be determined from the properties of the bead. Examples of possible properties which may be used to identify the batch to which a reporter bead belongs include, but are not necessarily limited to, (i) colour; (ii) fluorescence signal; (iii) infrared spectrum; (iv) radioactive tag and (v) detectable physical feature inclusive of size.

Figure 3:
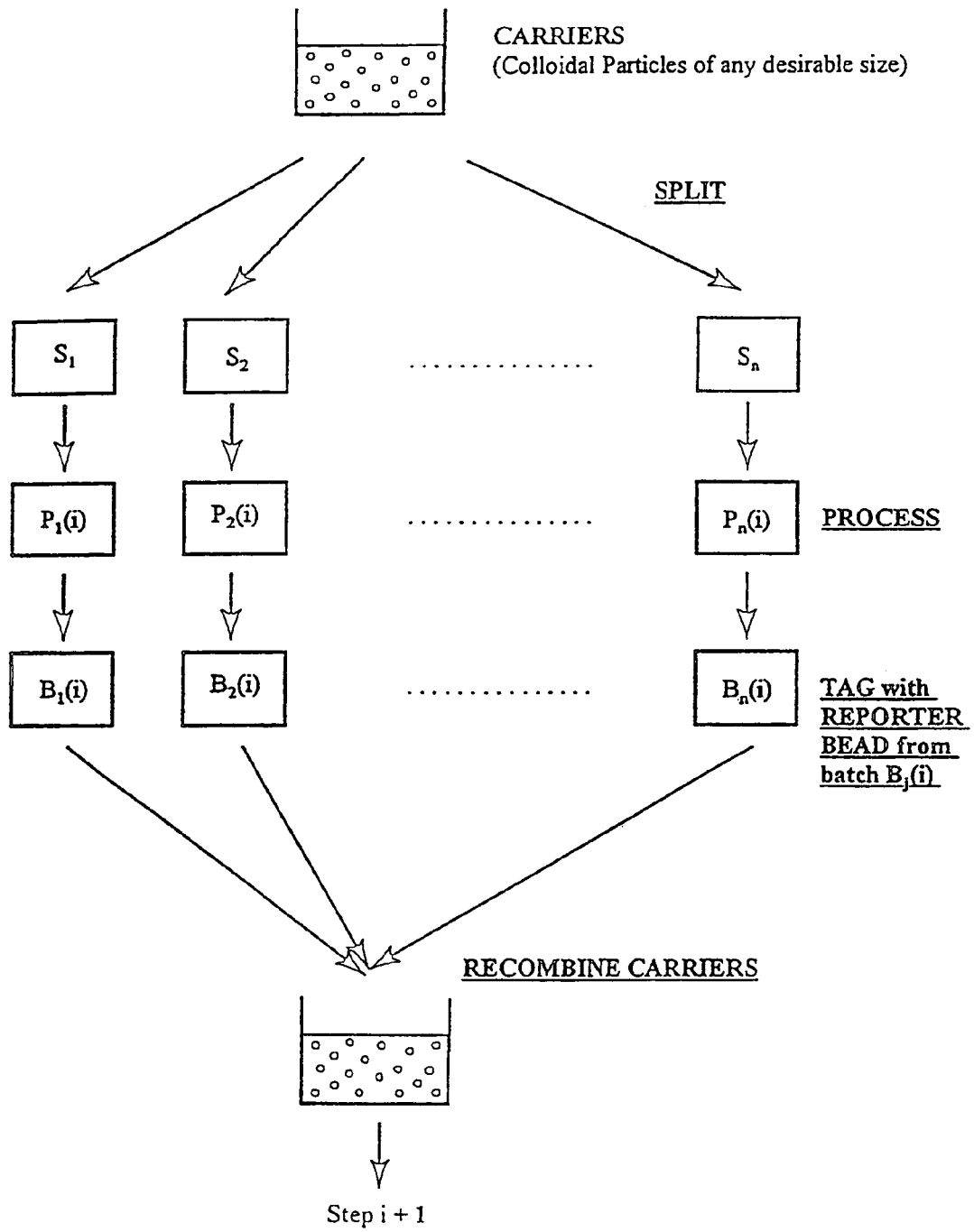
FIG. 3 is a schematic representation of one step in the split-process-recombine procedure of the invention which includes reporter bead tagging.

At each stage i in the procedure, one or more reporter beads from batch $B_j(i)$ is attached to each of the carriers which go through process $P_j(i)$. Then at the conclusion of the procedure, the sequence of processes applied to any particular carrier can be determined from the reporter beads which are attached to it as described hereinafter. The order of steps for this is shown schematically in FIG. 3.

An example of a method for attaching the reporter beads to the carrier beads is as follows. Note that it is possible to attach the reporter beads from batch $B_j(i)$ to the carriers before the process $P_j(i)$ is performed if this is desirable.

Figure 4:
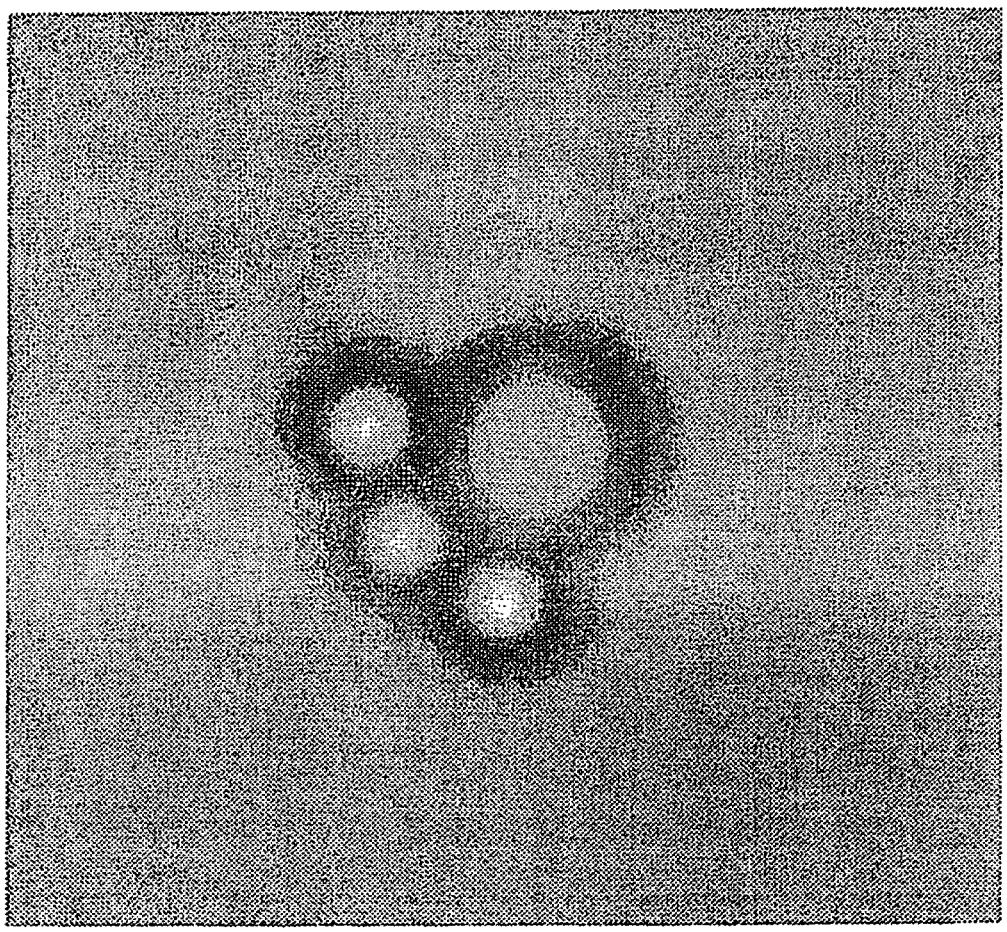
FIG. 4 is an illustrative example of reporter beads attached to a carrier particle wherein there is shown an optical microscope image of three 0.9 μm silica reporter beads attached to a 2.5 μm silica carrier bead. In this case, attachment was achieved by dissolving NaCl to a mixed aqueous suspension of these particles. The size of reporter beads would typically be much smaller than that of the carrier bead. The image is simply an illustrative example.

Most of the systems described above may utilize insoluble polystyrene or silica colloidal particles as carriers. In one example, we used a 2.5 µm silica particle as the carrier and 0.9 µm silica particles (obtained from Bangs Laboratories, Carmel, Ind., USA) as reporters. When suspended in aqueous solution (e.g., in Milli-Q ion exchanged water), these particles remain separate from each other by virtue of electrostatic repulsion forces which result from the negative surface charge on each particle. The dissolution of salt (e.g., sodium chloride) in the aqueous solution shields the effect of the electrostatic repulsion between the particles and results in a permanent coagulation (i.e., sticking) of the small particles with the large particles (see FIG. 4). Under such conditions, the adhesion of the small particles to the large particles is primarily caused by van der Waals attractive forces which occur between the particles (Hunter supra and Russel et al., supra. Moreover, as has been shown by Healy et al., (1966, Transactions of the Faraday Society 62 1638; 1970, ibid, 66 490), the rate of coagulation of small particles with large particles will always be greater than that of large particles with large particles or small particles with small particles. In an analogous way, the small particles can be attached to the large particles by using a combination of both electrostatic and van der Waals attractive forces. This is the situation for example if the small and large particles are oppositely charged. In such a situation, when a suspension of small particles is mixed with a suspension of large particles, coagulation (permanent adhesion) of small particles to large particles, and vice versa, will occur spontaneously. Such methods of coagulating mixtures of colloidal particles by utilizing physical/chemical interactions are well known to the art and are described in references which include the Hunter reference referred to above. In order to enhance the strength and selectivity of the particle-particle adhesion, chemical additives (e.g., polyelectrolytes) and chemical reactions (e.g., polymer bridging reaction between particles) may be used, however these are not essential. Indeed, as described above, there are significant advantages to tagging the carrier beads with physically attached tags, rather than chemically attached tags.

It will be appreciated that reporter beads may be attached to the surface of a carrier but this is not essential. In this regard, the inventors recognise that it would be possible to attach reporter beads to the inside of a carrier through existing pores of the carrier.

We note that it may be desirable to attach reporter beads to existing reporter beads on the carrier rather than directly onto the surface of the carrier. This may be advantageous in locating the reporter beads during the decoding procedure or it may give extra information as to the order in which the reporter beads were attached. This can be accomplished by utilizing intrinsic physical forces between the reporter beads. One example of how this can be accomplished is to alternate the surface charge on the reporter beads. For example, the first reporter beads to be attached to the carrier particles will have either positive or negative surface charge. The next batch of reporter beads will possess the opposite charge to those previously attached (i.e., positive for negatively charged reporter beads in the first tagging step and vice versa). Altering the surface charge of the reporter beads in this manner will allow reporter beads to attach to other reporter beads as well as to the carrier particles.

It is desirable that any reporter beads which are left in solution (i.e., those which do not attach to a carrier) be removed from the solution before the next step in the procedure. This can be achieved, for example, by allowing the heavier carrier beads to settle to the bottom and removing any non-attached reporter beads by decanting of the solution containing the suspended reporter beads and rinsing with clear solution. To aid this procedure, a charged plate of opposite polarity to that of the carrier beads may be used to attract the carrier beads (with attached reporter beads) whilst repelling the unattached reporter beads.

An example of how reporter bead attachment can be used to determine the sequence of processes performed on any carrier bead is illustrated below.

Let us consider a process which contains 4 steps (i=1, . . . , 4) and 4 processes (j=1, . . . , 4). For example, a 4-step combinatorial oligopeptide synthesis. Each step involves the addition of one amino acid monomer, of a set of four amino acids which are of interest (e.g. alanine, glycine, lysine and methionine). Each process defines which of the 4 possible amino acid monomers is attached. After 4 steps, each carrier will contain a oligopeptide chain with 4 amino acid monomers in random sequence. In this case, the total possible number of sequences is $4^4$ (=256).

In order to tag each step and each process uniquely, we need 16 types of reporter beads which will be attached to the carriers before or after each step (according to FIG. 3), and can be later uniquely identified. The simplest way of achieving this is to use reporter beads (e.g., 1 µm silica beads) which contain a combination of 4 fluorescent dyes in their interior.

Four convenient fluorescent dyes are Red (R), Yellow (Y), Green (G) and Blue (B). With 4 dyes, there are 16 possible combinations of dye colours which can be incorporated in the reporter beads (i.e., RYGB, RYG, RGB, RYB, YGB, RY, RG, RB, YG, YB, GB, R, Y, G, B, no dye) and so 16 different batches of reporter beads can be manufactured. By attaching one of these beads to the carrier immediately before or after an amino acid addition, the combination of dyes within the reporter bead will code for one unique process and step (i.e., it will define $P_j(i)$ in FIG. 3).

Detection of the dye combination within the beads can conveniently be achieved with a fluorescence microscope after the entire process is complete. The microscope will have sufficient magnification to observe the individual reporter beads, and appropriate light filters can be used to determine which fluorescent colours (if any) are being emitted from the reporter beads attached to the carrier. Having regard to the above example, if each carrier contains a oligopeptide chain of 4 amino acid monomers, there will be four distinct reporter populations attached to each carrier. This means that once 4 distinct reporter beads are identified on a carrier, the sequence of reaction steps experienced by that carrier is uniquely determined.

Generally, for a split-process-recombine procedure with m steps and n processes, a set of m×n batches of reporter beads is sufficient to uniquely tag the entire process. In the above example, we showed how 16 unique tags could be produced from a combination of 4 fluorescent dyes. This number can be vastly increased by a number of simple schemes:—

Figure 5:
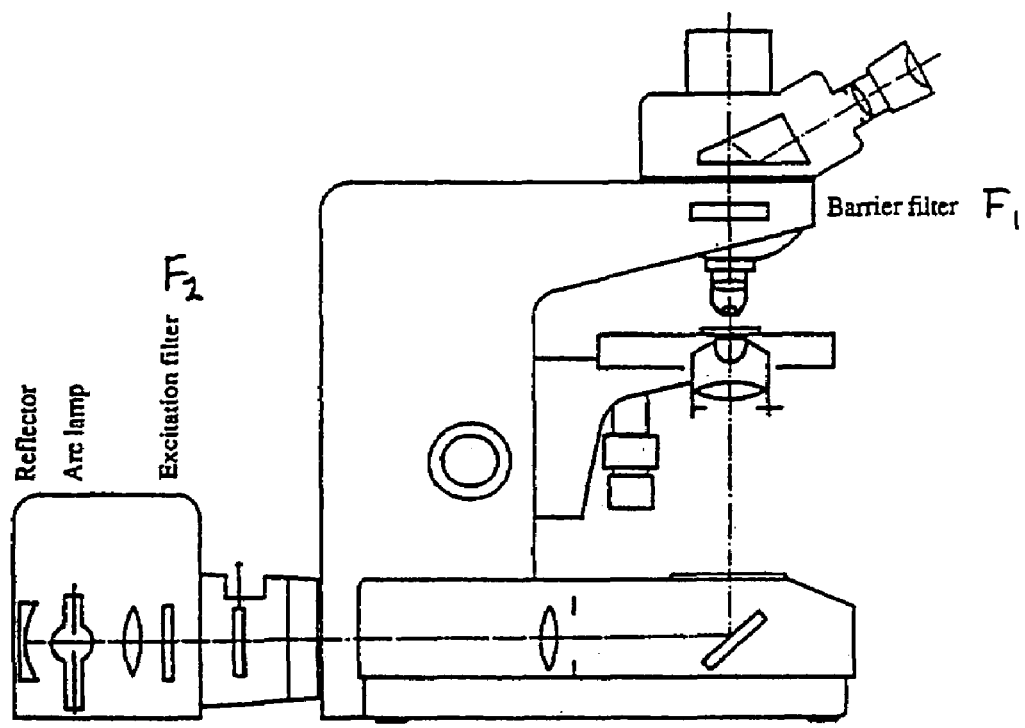
FIG. 5 is a schematic of the fluorescence microscope apparatus which may be used for the decoding experiments. The barrier filter ($F_1$) and the excitation filter ($F_2$) are clearly labelled.

(I) Increase the number of fluorescent dyes, with distinct fluorescent signals, incorporated inside the reporter particle. This can be achieved not only by choosing dyes with clearly distinct emission frequencies, but also by choosing dyes with similar emission frequencies, but with clearly distinct excitation frequencies. Fluorescent optical microscopy techniques are available for this purpose (as described in *Fluorescent Microscopy* by F. W. D. Rost, Cambridge University Press, Vol. 1, 1992 and *Introduction to Fluorescent Microscopy* by J. S. Ploem and H. J. Tanke, Oxford University Press, 1987). FIG. 5 illustrates how the microscope can be set up. Two particle dyes with similar emission frequencies can be distinguished because of their distinct excitation frequencies. Suppose one dye D1 emits red light after excitation with green light and another dye D2 emits red light after excitation with blue light. The microscope set-up shown in the diagram can distinguish the two dyes by changing the filter $F_2$ to transmit only green light or only blue light. The dye D1 will emit red light only when green light is passed through $F_2$. The dye D2 will emit red light only when blue light is passed through $F_2$. Different coloured dyes within the particles can be detected by changing the transmitting frequency of filter $F_1$. Judicious choice of such dyes will increase the number of reporter dyes from 4 to greater than 20.

(II) The size of the reporter bead can be varied in order to increase the possible number of tags. (e.g., if two different sizes are used for reporter beads, the number of possible tags is doubled)

(III) The concentration of fluorescent dye within each reporter bead can be varied. Different concentrations will give rise to different emission intensities (e.g., two different dye concentrations within the reporter beads will double the number of possible tags).

The capacity of this technique to determine the sequence of reaction steps when larger numbers of processes and steps are involved is clearly demonstrated by the following argument. If x different fluorescent dyes can be incorporated in a reporter bead then the number of different batches of reporter beads which can be manufactured is $2^x$. With $2^x$ distinct batches of reporter beads it is possible to trace the sequence of reaction steps performed on a carrier provided the product n×m of the number of processes with the number of steps is less than $2^x$. Even though the number of possible sequences of reactions performed on a carrier is $n^m$, the technique requires at most $\log_2(n \times m)$ different dyes. This value or number is rounded out to the nearest integer above or equal to this value. For example, if 20 processes (as would be the case for 20 amino acids involved in polypeptide synthesis) and 25 reaction steps are involved then there are $20^{25} \approx 3 \times 10^{32}$ possible sequences but only 9 different dyes are required.

Although this example specifies fluorescence as the detection method for the reporter beads, many other reporting and detection methods can also be envisaged. Examples of these include doping the reporter beads with materials which have unique infrared and radioactive signals. These could be used either independently, or in combination with the fluorescent reporter molecules.

For the 4×4 combinatorial oligopeptide synthesis described above, the following procedure as described in Example 1 is used to synthesize and tag.

EXAMPLE

Example 1

Carrier beads used for this procedure are N-α-Boc (t-butyl oxy carbonyl) protected amino acid 4-hydroxymethylphenylacetamidomethyl resin (PAM-resin) (available from Novabiochem). These carrier particles (100-200 mesh) are a standard support for solid phase combinatorial synthesis. In this example, we chose the N-α-Boc-Ala-OCH$_2$-4-hydroxymethylphenylacetamidomethyl resin (PAM resin) which contains a protected alanine amino acid residue attached to the surface (other amino acid residues may also be chosen to begin the sequence). All synthesis steps in the split-process-recombine procedure were carried out on a 0.2 mmol scale as follows. The N-α-Boc group was removed by treatment with 100% TFA (trifluoro acetic acid) for 2×1 minute followed by a 30 second flow wash with DMF (dimethyl formamide). Boc amino acids (0.8 mmol) were coupled, without prior neutralization of the peptide-resin salt, as active esters preformed in DMF with either hydroxy benzyl triazol (HOBt)/N,N'-diisopropyl carbodiimide (DIC) (30 minutes activation), or a HBTU/diisopropyl ethyl amine (DIEA) (2 minutes activation) as activating agents. For couplings with active esters formed by HOBt/DIC, neutralization was performed in situ by adding 1.5 equiv. DIEA relative to the amount of TfaO$^-$—$^+$NH3-peptide-resin salt to the activated Boc-amino acid resin mixture. For couplings with active esters formed from HBTU/DIEA, an additional 2 equiv. DIEA relative to the amount of TfaO$^{-+}$NH3-peptide-resin salt were added tot the activation mixture. Coupling times were 10 minutes throughout without any double coupling. Samples (3-5 mg) of peptide resin were removed after the coupling step for determination of residual-amino groups by the quantitative ninhydrin method. Coupling yields are typically 99.9%. All operations were performed manually in a 20 mL glass reaction vessel with a telfon-lined screw cap. The peptide-resin was agitated by gentle inversion on a shaker during the N-α-deprotection and coupling steps. Prior to recombining and splitting the beads according to the diagram in FIG. 2, reporter beads (1 μm diameter silica particles) were attached to the resin-peptide carrier beads via the procedures described above (i.e., coagulation in aqueous solution induced with high concentrations (approximately 1 molar) of sodium chloride salt). After peptide additions (i.e., 4-steps) reporter particles remained adhered to the carrier beads.

As well as this limiting example of combinatorial polypeptide synthesis, our coding/decoding method is generally applicable to all solid phase combinatorial chemistry. Other examples of such processes include polynucleotide and cyclic polypeptide synthesis.

Example 2

Preparation of Reporter Suspensions

Fluorescent silica microspheres (10 mg, 1 μm diameter, red or blue or green or yellow/red combination, Microcaps) are coated with polyelectrolytes. The first step is to coat the silica with positively charged polyethyleneimine (PEI) by sonicating for 30 minutes in a 1% aqueous solution of PEI (3 ml, Polysciences Inc., MWt=10000 g/mol) and equilibrating for 24 hours. After washing with reverse osmosis (RO) water (MILLI-Q) by centrifugation (5×3 ml), the silica is added to a 1% aqueous solution of negatively charged polyacrylic acid (PAA, 3 ml, Sigma-Aldrich, MWt=250000 g/mol), equilibrated for 24 hours and washed with RO water (MILLI-Q) by centrifugation (5×3 ml).

The polyelectrolyte coated silica beads are washed with dimethylformamide (i.e., DMF) (5×10 ml) and used as a suspension in DMF (10 mg/ml).

Example 3

Preparation of a Tagged Library

Procedure A: Tagging the Carrier Beads

Cross-linked PS/DVB dry resin beads (aminomethylated, 75-150 μm in diameter, 200 mg, 0.26 mmol/g, Peptide Institute) is split into two 100 mg portions.

One portion is mixed with 0.25 ml of red polyelectrolyte-coated silica reporters (10 mg/ml) in DMF (Population 1) and, similarly, the other portion is added to 0.250 ml green polyelectrolyte-coated silica reporters 910 mg/ml) in DMF (Population 2). Refer to Example 2 for preparation of polyelectrolyte-coated silica reporters.

Procedure B:

The resin is washed with excess DMF (20×20 ml). The solvent and free reporters are removed by vacuum filtration through a glass sinter of pore size 17-40 μm. After the final wash, the resin remains in DMF.

Procedure C:

The monomer Fmoc-Glycine-OH (150 mg, 0.5 mmol, Novabiochem) is mixed with N-[1H-(benzotriazol-I-yl) (dimethylamino)methylene]-N-methylmethanaminimum hexafluorophosphate N-oxide (HBTU, 0.5 mmol, 0.5 M, 1 ml) and diisopropylethylamine (DIEA, 0.6 mmol, 120 μl). The activated amino acid is added to the beads (100 mg) of Population 1 as prepared in Procedure B and shaken for 10 minutes. The resin is washed with DMF (5×20 ml).

The second monomer Fmoc-Alanine-OH (160 mg, 0.5 mmol, Novabiochem) is mixed with HBTU (0.5 mmol, 0.5 M, 1 ml) and DIEA (0.6 mmol, 130 μl). The activated amino acid is added to the beads (100 mg) of Population 2 as prepared in Procedure B and shaken for 10 minutes. The resin is washed with DMF (5×20 ml).

Figure 6:
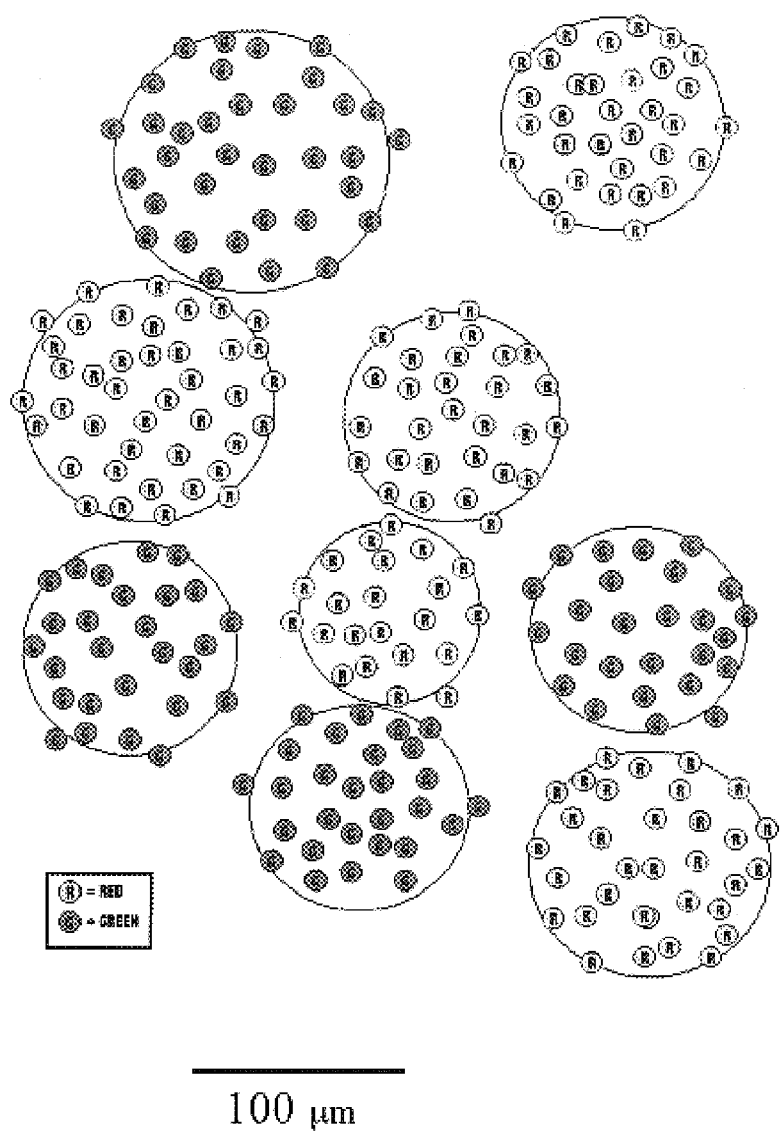
FIG. 6 is a schematic diagram of red-tagged and green-tagged carriers, combined to form Population 3 in Procedure D in Example 3 hereinafter. For clarity, the reporters drawn here are much larger than the 1 μm reporters used in the Example.

Procedure D:

Population 1 in DMF is combined with Population 2 in DMF to become Population 3, a mixture of red-tagged and green-tagged resins. Population 3 is shaken in DMF for 1 minute to ensure good mixing. FIG. 6 is a schematic of the red-tagged and green-tagged beads in Population 3. Population 3 is split into two 100 mg portions, Population 4 and Population 5.

Figure 7:
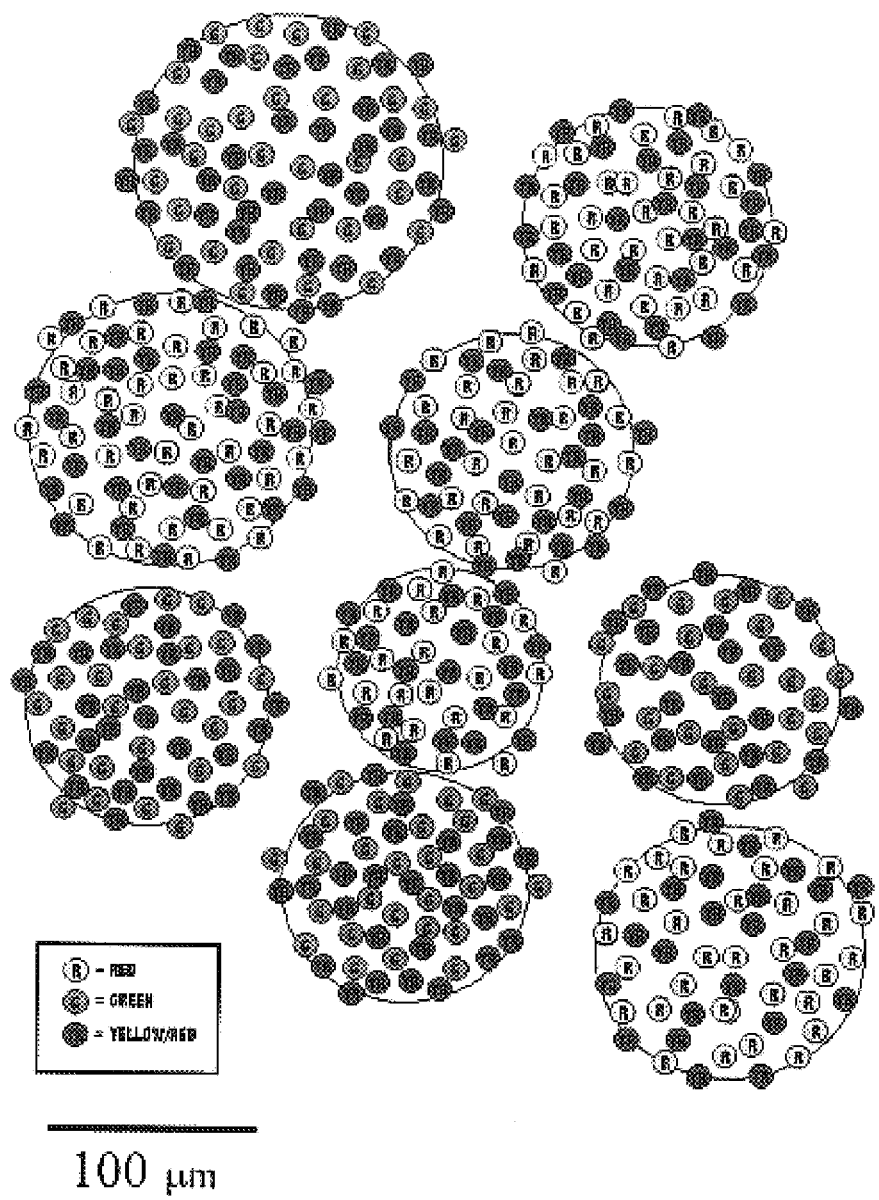
FIG. 7 is a schematic diagram of Population 4 in Procedure E in Example 3. For clarity, the reporters drawn here are much larger than the 1 μm reporters used in the Example.

Procedure E:

A 1 ml suspension of fluorescent yellow/red polyelectrolyte-coated reporters in DMF (10 mg/ml, as prepared in Example 2) is shaken with Population 4 and 1 ml piperidine for 5 minutes. The solvent is removed and a fresh solution of reporters in piperidine/DMF is shaken with the carriers for another 5 minutes. A schematic of Population 4 is shown in FIG. 7.

Figure 8:
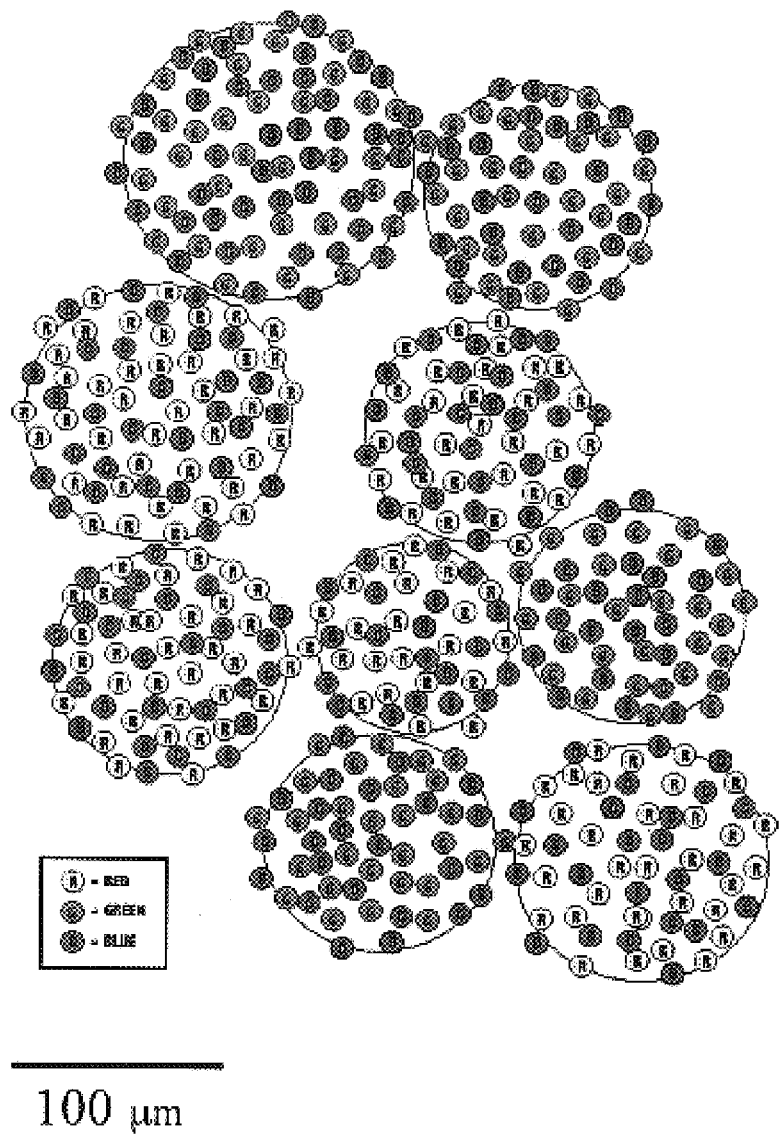
FIG. 8 is a schematic diagram of Population 5 in Procedure E in Example 3. For clarity, the reporters drawn here are much larger than the 1 μm reporters used in the Example.

A 1 ml suspension of fluorescent blue polyelectrolyte-coated reporters in DMF (10 mg/ml, as prepared in Example 2) is shaken with Population 5 and 1 ml piperidine for 5 minutes. The solvent is removed and a fresh solution of reporters in piperidine/DMF is shaken with the carriers for another 5 minutes. A schematic of Population 5 is shown in FIG. 8.

Populations 4 and 5 are washed separately with copious amounts of DMF (20×20 ml each) to remove excess reporters.

Figure 9:
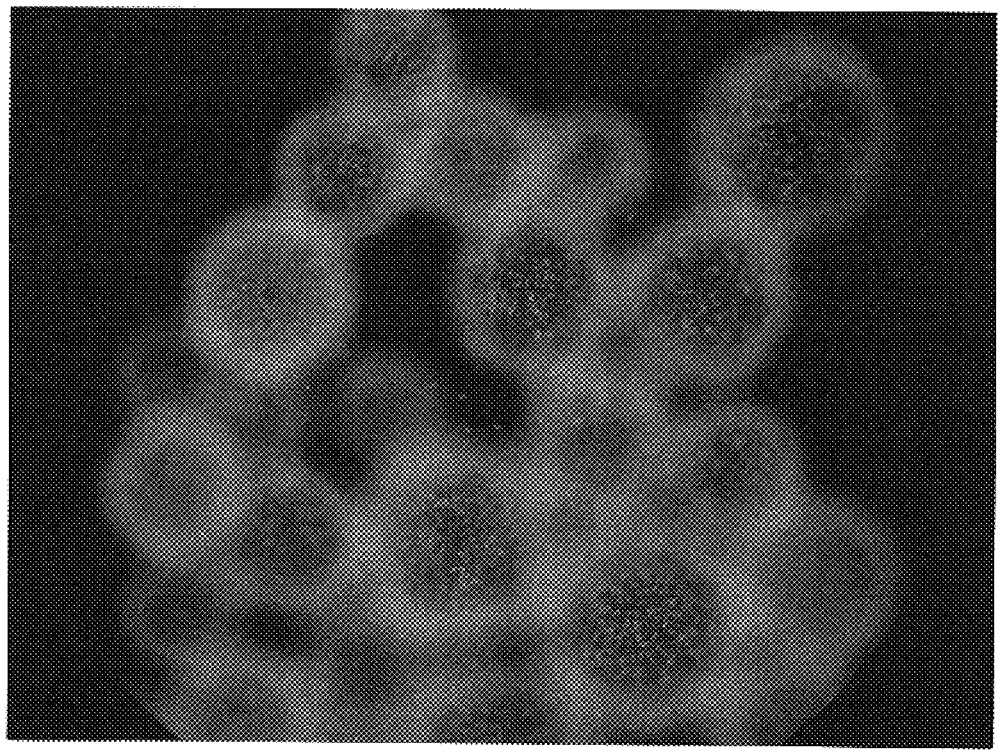
FIG. 9 shows two fluorescence microscopy images (as FIG. 9(a) and FIG. 9(b)) of a sample of carrier beads after the second tagging and coupling step (a sample of Population 4 in Procedure F in Example 3)
Figure 9:
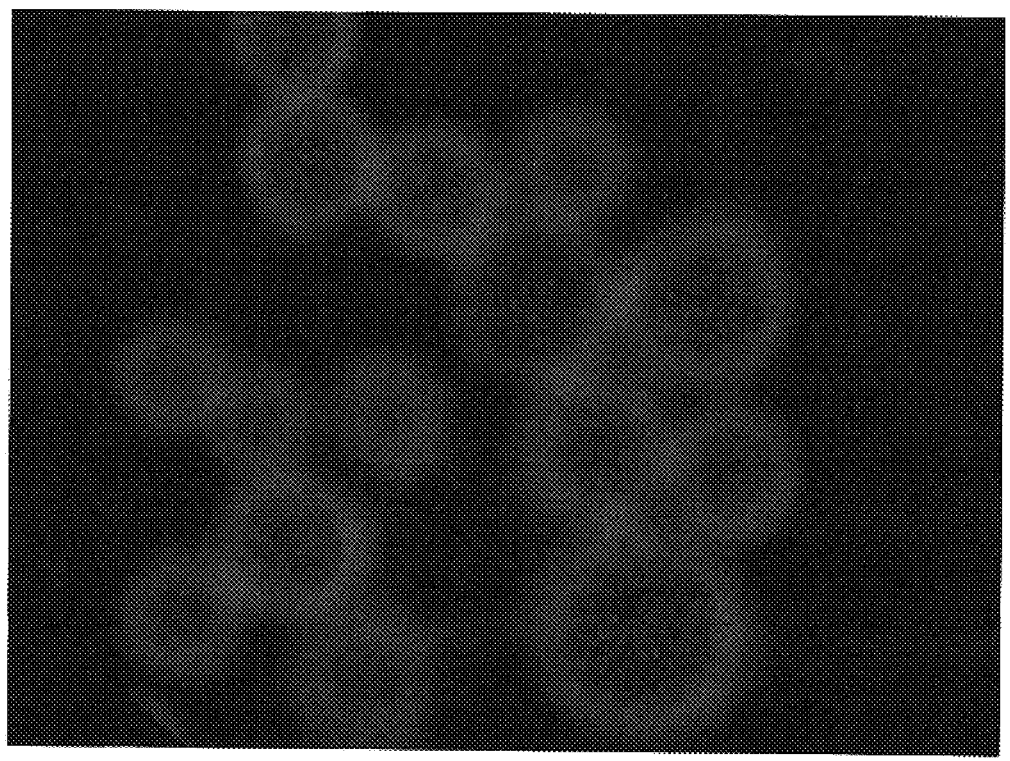

Procedure F:

The monomer FMOC-Lysine(Boc)-OH (235 mg, 0.5 mmol, Novabiochem) is mixed with HBTU (0.5 mmol, 0.5 M, 1 ml) and DIEA (0.6 mmol, 120 μl). The activated amino acid is added to the beads (100 mg) of Population 4 as prepared in Procedure E and shaken for 10 minutes. The resin is washed with excess DMF (5×20 ml). The relevant images are shown in FIG. 9.

In the procedure of obtaining the images referred to in FIGS. 9(a) and 9(b), one species of carrier is tagged with green and yellow/red corresponding to the sequence Lysine-Alanine-carrier and the other species of carrier present is tagged with red and yellow/red reporters-corresponding to the peptide sequence Lysine-Glycine-carrier.

In the top micrograph (a), the sample is excited with blue light ($\lambda$=450-480 nm) and emission wavelengths below $\lambda$=515 nm are filtered out so that only wavelengths above $\lambda$=515 nm are observed.

The predominantly green carriers in (a) are those which have been tagged with fluorescent green reporters in Procedure A in Example 3) and fluorescent yellow/red reporters in Procedure E in Example 3. Higher magnification allows clearer observation of individual fluorescent green and fluorescent yellow reporter beads; the latter being the yellow signals from each combined yellow/red reporter.

The predominantly yellow carriers in (a) are those which have been tagged with fluorescent red reporters in Procedure A in Example 3 and fluorescent yellow/red reporters in Procedure E in Example 3. Higher magnification allows clearer observation of individual fluorescent red and fluorescent yellow reporter beads; the latter being the yellow signals from each combined yellow/red reporter.

In the lower micrograph (b), the sample is excited with green light ($\lambda$=510-550 nm) and emission wavelengths below $\lambda$=590 nm are filtered out so that only wavelengths above $\lambda$=590 nm are observed.

The darker (less red) carriers in (b) are those which have been tagged with fluorescent green reporters in Procedure A in Example 3 and fluorescent yellow/red reporters in Procedure E in Example 3. The fluorescent green reporters cannot be observed under this excitation but the red signal from the combined yellow/red reporters can be observed.

The brighter (more red) carriers in (b) are those which have been tagged with fluorescent red reporters in Procedure A in Example 3 and fluorescent yellow/red reporters in Procedure E in Example 3. The fluorescent red reporters can be distinguished from the combined yellow/red reporters because the red fluorescence from each red reporter is duller than the red fluorescence from each combined yellow/red reporter.

The monomer FMOC-Arginine(PMC)—OH (304 mg, 0.5 mmol, Bachem) is mixed with HBTU (0.5 mmol, 0.5 M, 1 ml) and DIEA (0.6 mml, 120 μl). The activated amino acid is added to the beads (100 mg) of Population 5 as prepared in Procedure E and shaken for 10 minutes. The resin is washed with excess DMF (5×20 ml). The relevant images are shown in FIGS. 10(a), 10(b) and 10(c).

Figure 10:
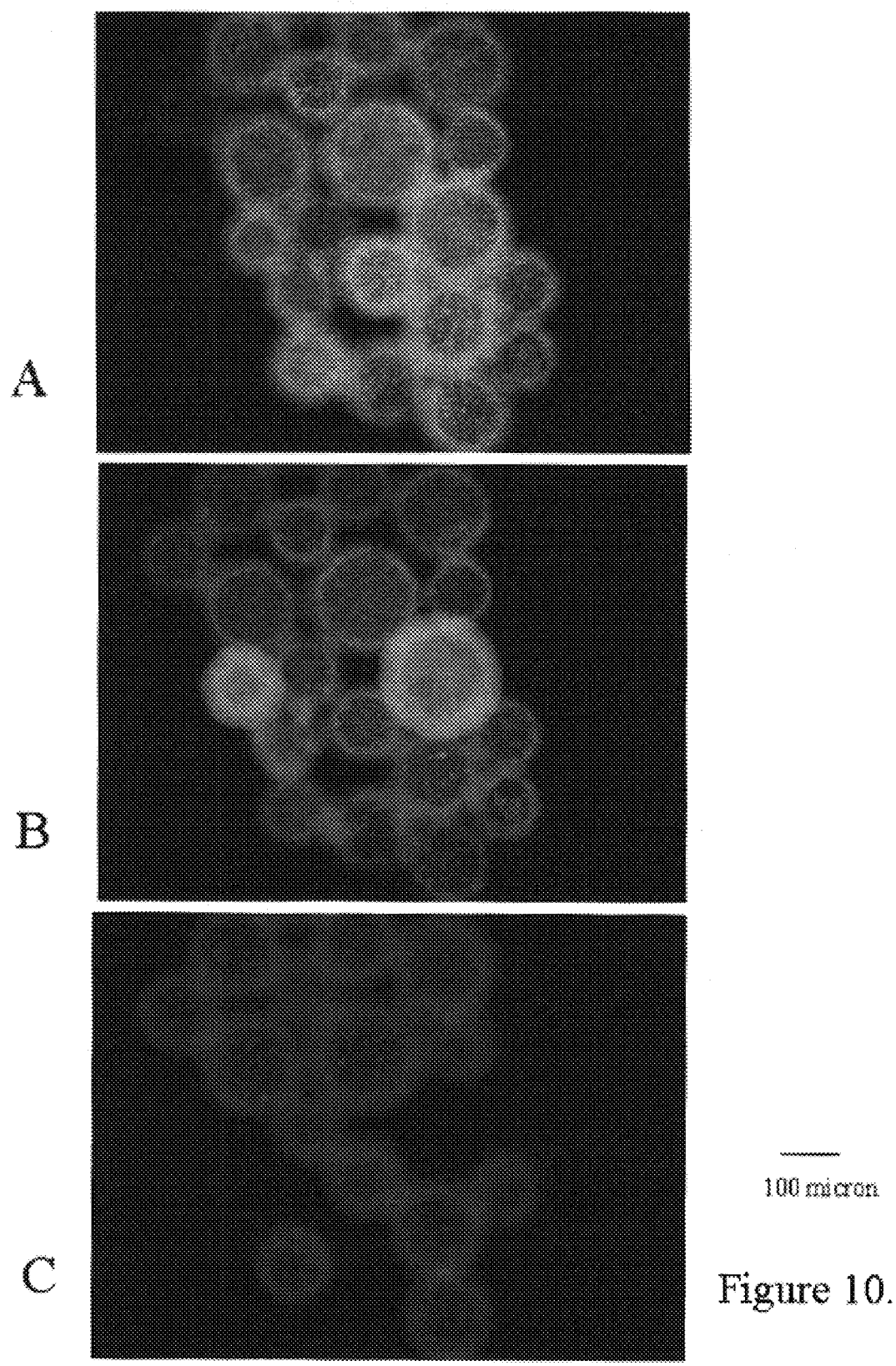
FIG. 10 shows three fluorescence microscopy images (as FIGS. 10(a), 10(b) and 10(c)) of a sample of carrier beads after the second tagging and coupling step (a sample of Population 5 in Procedure F in Example 3)

In the procedure of obtaining the images referred to in FIG. 10, one species of carrier is tagged with red and blue reporters corresponding to the peptide sequence Arginine- Glycine-carrier and the other type of carrier present is tagged with green and blue corresponding to the sequence Arginine-Alanine-carrier.

In the top micrograph (a), the sample is excited with light of wavelength ($\lambda$=330-385 nm) and emission wavelengths below $\lambda$=420 nm are filtered out so that only wavelengths above $\lambda$=420 nm are observed.

The green/aqua carriers in (a) are those, which have been tagged with fluorescent green reporters in Procedure A in Example 3 and fluorescent, blue reporters in Procedure E in Example 3. Higher magnification allows clearer observation of individual fluorescent green and fluorescent blue reporter beads.

The red/pink carriers in (a) are those, which have been tagged with fluorescent red reporters in Procedure A in Example 3 and fluorescent, blue reporters in Procedure E in Example 3. Higher magnification allows clearer observation of individual fluorescent red and fluorescent blue reporter beads.

In micrograph (b), the sample is excited with blue light ($\lambda$=450-480 nm) and emission wavelengths below $\lambda$=515 nm are filtered out so that only wavelengths above $\lambda$=515 nm are observed.

The predominantly green carriers in (b) are those, which have been tagged with fluorescent green reporters in Procedure A in Example 3 and fluorescent blue reporters in Procedure E in Example 3. Higher magnification allows clearer observation of individual fluorescent green reporter beads. The fluorescent blue reporters cannot be observed under this excitation.

The predominantly yellow carriers in (b) are those, which have been tagged with fluorescent red reporters in Procedure A in Example 3 and fluorescent blue reporters in Procedure E in Example 3. Higher magnification allows clearer observation of individual fluorescent red reporter beads. The fluorescent blue reporters cannot be observed under this excitation.

In the lower micrograph (c), the sample is excited with green light ($\lambda$=510-550 nm) and emission wavelengths below $\lambda$=590 nm are filtered out so that only wavelengths above $\lambda$=590 nm are observed.

The dark carriers in (c) are those, which have been tagged with fluorescent green reporters in Procedure A in Example 3 and fluorescent, blue reporters in Procedure E in Example 3. The fluorescent green and the fluorescent blue reporters cannot be observed under this excitation, and so the carriers which have been tagged with green and blue, appear dark.

The red carriers in (c) are those, which have been tagged with fluorescent red reporters in Procedure A in Example 3 and fluorescent, blue reporters in Procedure E in Example 3. Under higher magnification, the individual red reporters can be observed. The fluorescent blue reporters cannot be observed under this excitation.

Thus, the red carriers in (c) are predominantly yellow in (b) and red/pink in (a), and the dark carriers in (c) are predominantly green in (b) and green/aqua in (a).

Figure 11:
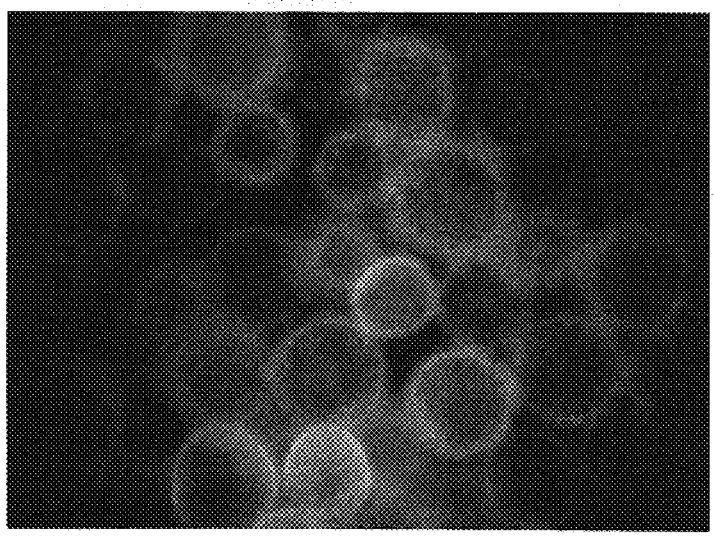
FIG. 11 shows three fluorescence microscopy images as FIGS. 11(a), 11(b) and 11(c) of a sample of carrier beads after the second tagging and coupling step (a sample of combined Population 4 and 5 in Procedure G in Example 3.
Figure 11:
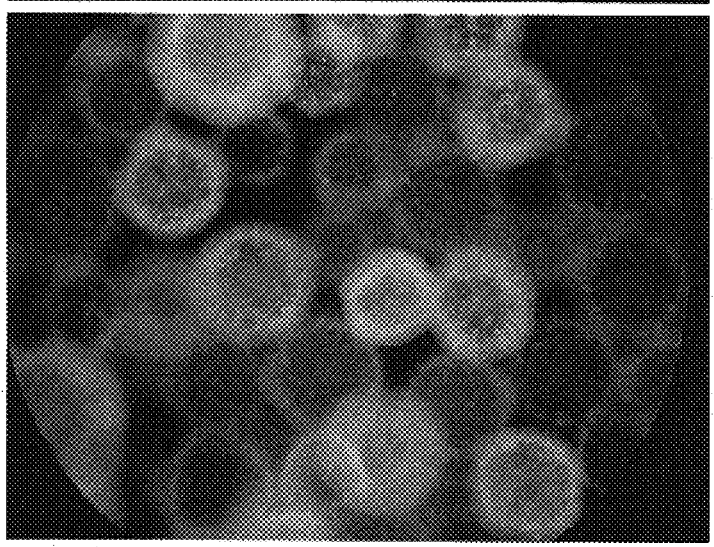
Figure 11:
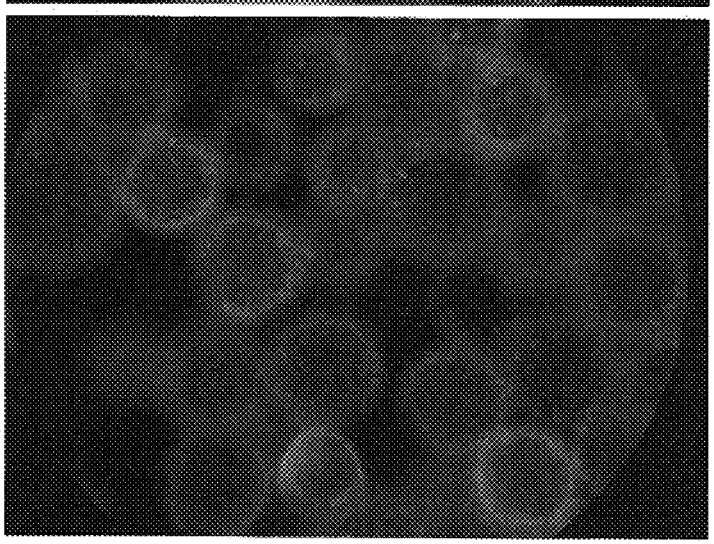
Figure 12:
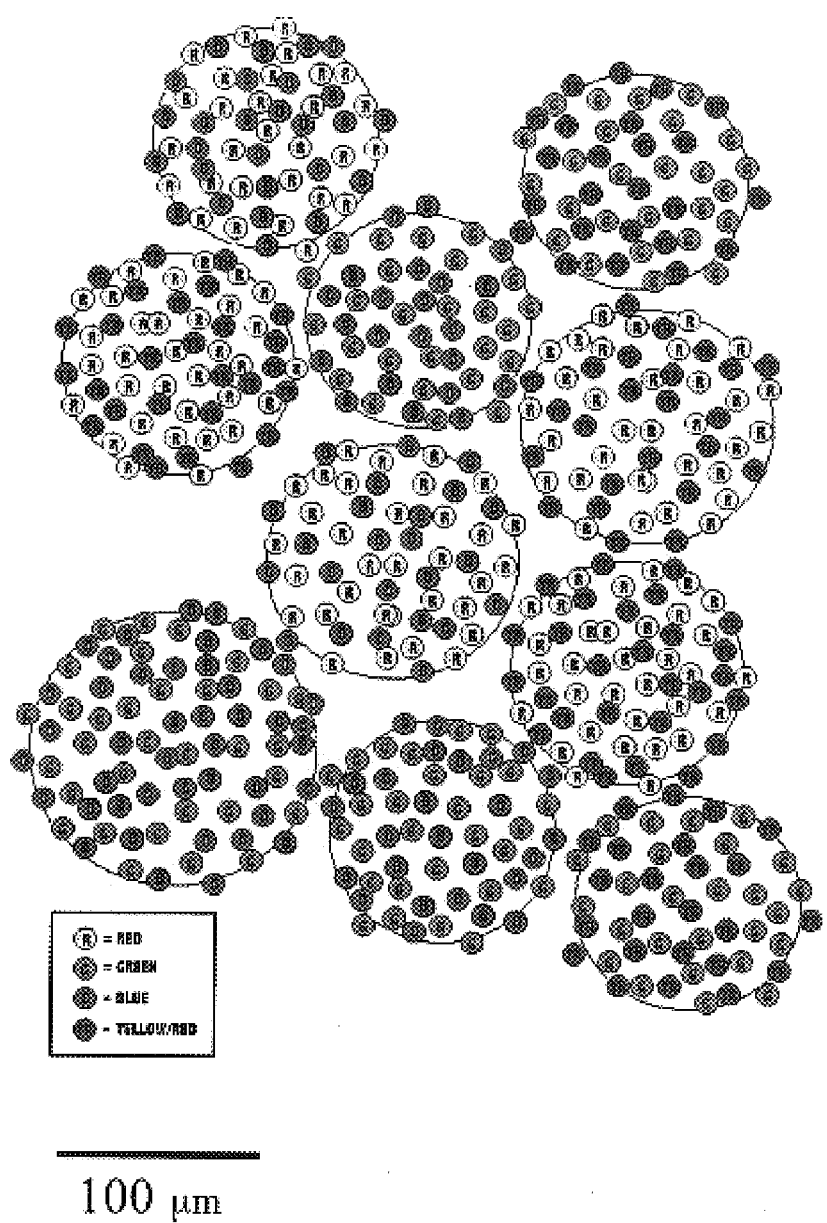
FIG. 12 is a schematic of combined Populations 4 and 5 in Procedure G in Example 3. For clarity, the reporters drawn here are much larger than the 1 μm reporters used in the Example.
Figure 13A:
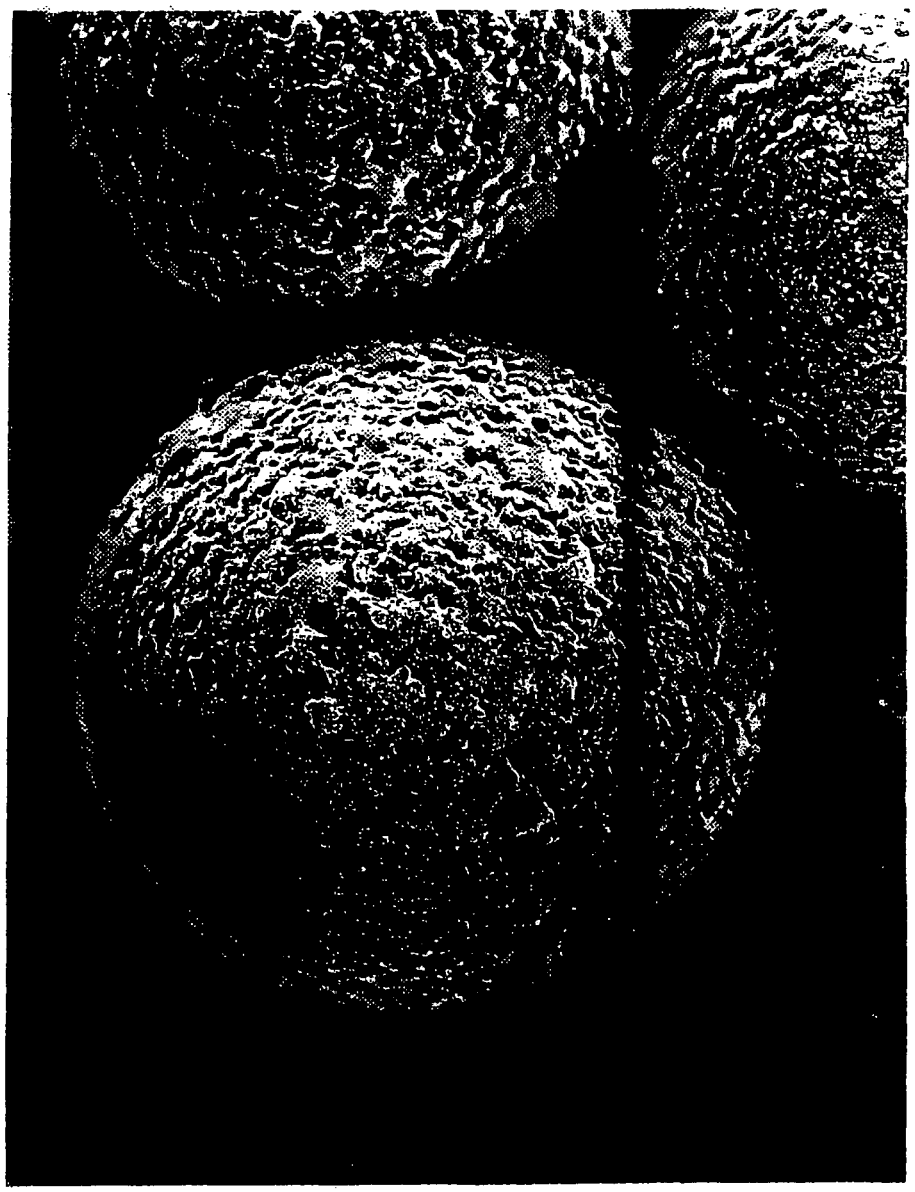
FIG. 13, as FIGS. 13(a) and 13(b), show scanning electron micrographs of 0.2 μm particles attached to aminomethylated (~100 μm) carriers, and (c) 2.5 μm polyelectrolyte coated silica particles attached to an aminomethylated (~100 μm) carrier.
Figure 13B:
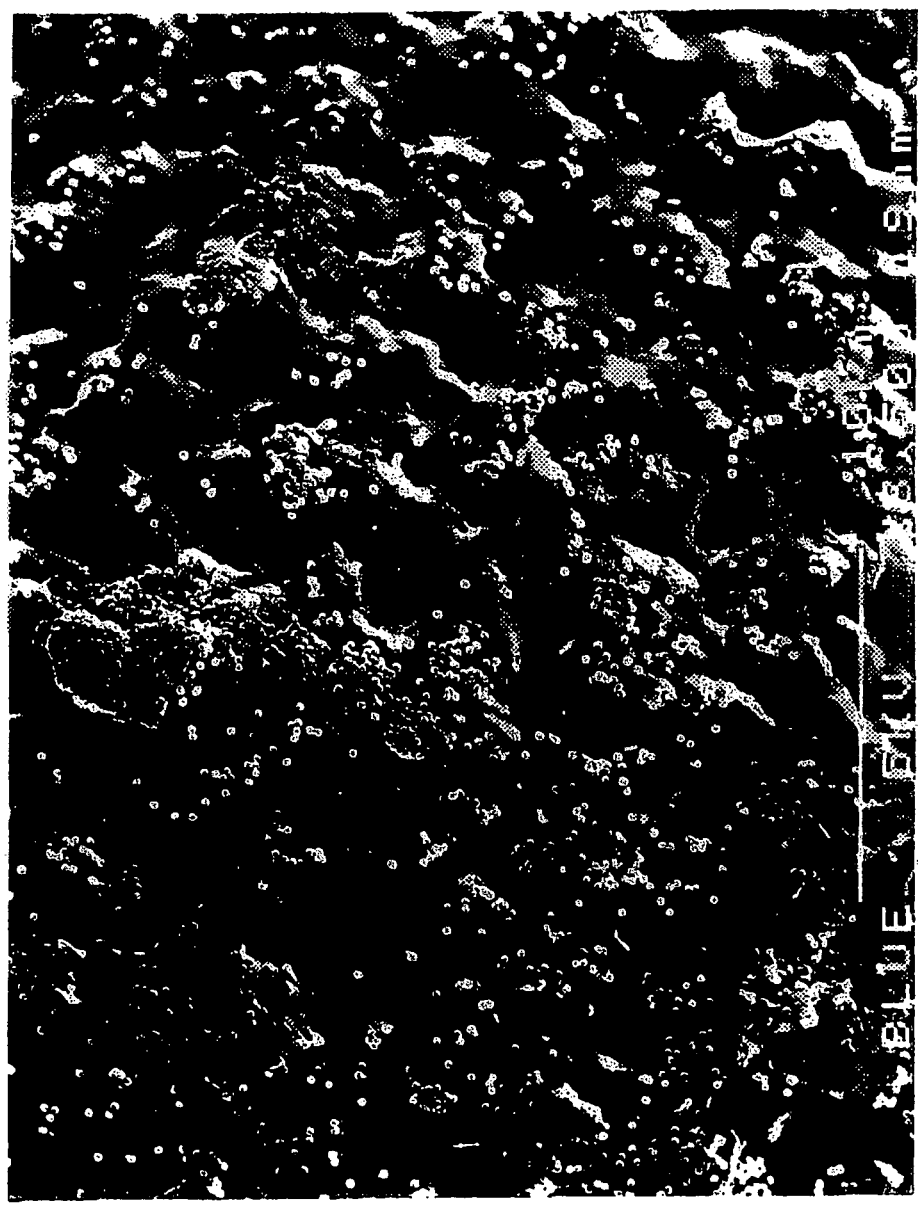
Figure 13C:
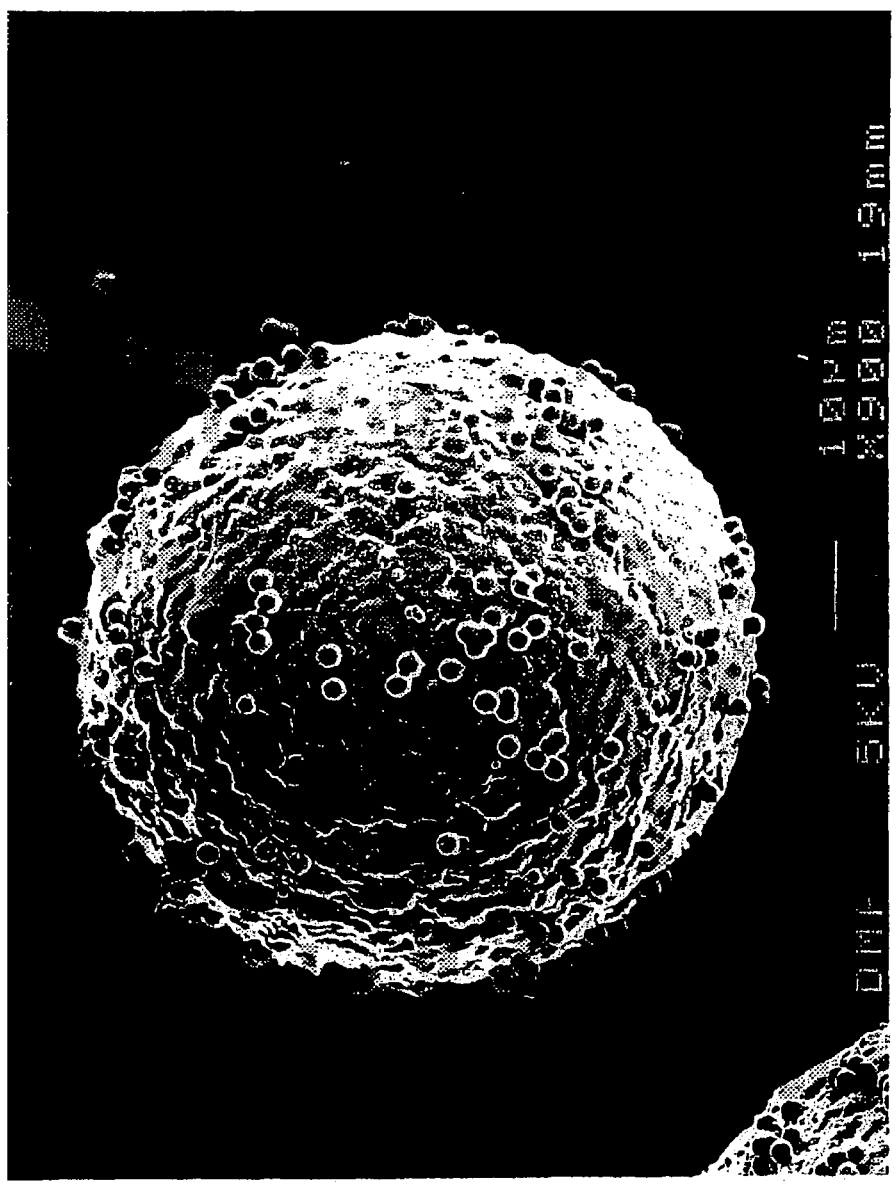
Figure 14:
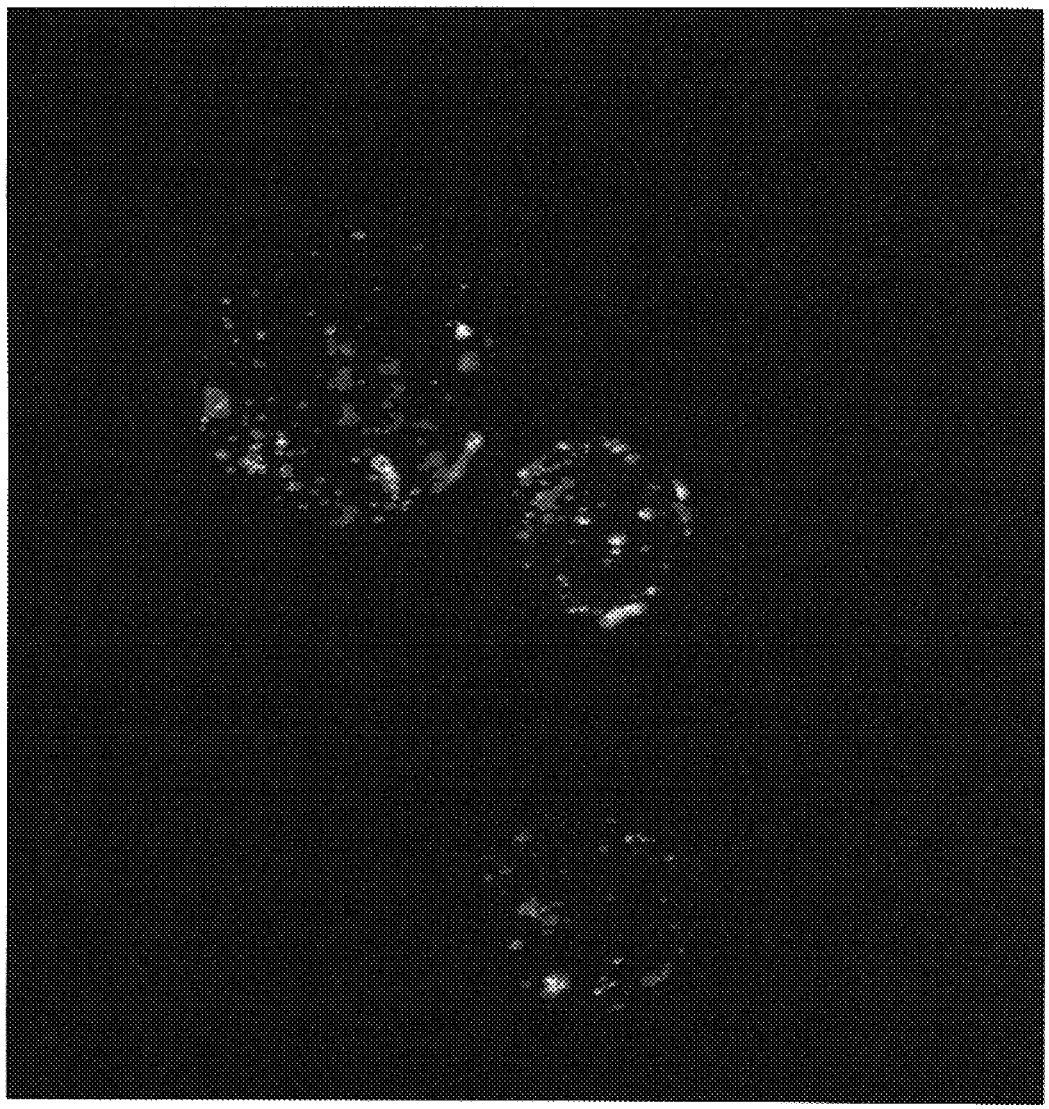
FIG. 14 shows a confocal fluorescence microscopy image of three carriers, each tagged with 1 μm fluorescent red, 1 μm fluorescent green and 2.0 μm far red fluorescent reporters. The red colours on the micrograph denote the red reporters, the green colours on the micrograph denote the green reporters and the blue colours on the micrograph denote the far red coloured reporters.
Figure 15:
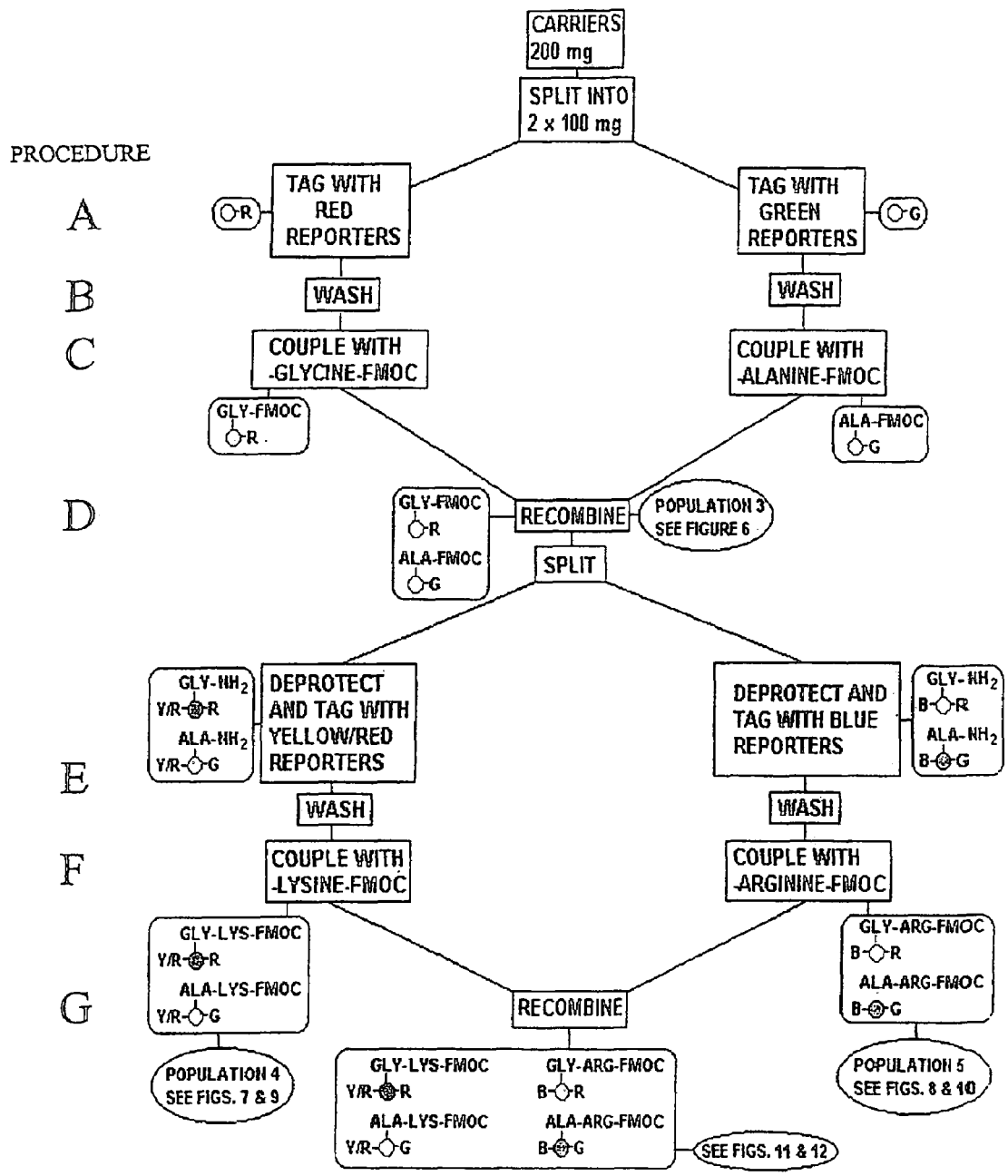
FIG. 15 is a schematic of the two step split-process-recombine method in Example 3.

Procedure G:

Populations 4 and 5 in DMF are combined. Refer to FIGS. 11(a), 11(b) and 11(c). A schematic view is shown in FIG. 12.

In relation to decoding the images shown in FIGS. 11(a), 11(b) and 11(c), the four differently-tagged carrier species are easily decoded. The four species of carrier are as follows. Carriers tagged with red and blue reporters correspond to the peptide sequence Arginine-Glycine-carrier; carriers tagged with green and blue correspond to the sequence Arginine-Alanine-carrier; carriers tagged with green and yellow/red correspond to the sequence Lysine-Alanine-carrier and carriers tagged with red and yellow/red reporters correspond to the peptide sequence Lysine-Glycine-carrier.

In the top micrograph (a), the sample is excited with light of wavelength ($\lambda$=330-385 nm) and emission wavelengths below $\lambda$=420 nm are filtered out so that only wavelengths above $\lambda$=420 nm are observed.

The red/pink carriers in (a) are those which have been tagged with fluorescent red reporters in Procedure A in Example 3 and fluorescent blue reporters in Procedure E in Example 3. Higher magnification allows clearer observation of individual fluorescent red and fluorescent blue reporter beads.

The bright red carriers in (a) are those, which have been tagged with fluorescent red reporters in Procedure A in Example 3 and fluorescent yellow/red reporters in Procedure E in Example 3.

The green/aqua carriers in (a) are those, which have been tagged with fluorescent green reporters in Procedure A in Example 3. Extra information is required (e.g. micrographs (b) and (c)] to distinguish between the carriers tagged with both green and blue reporters and the carriers tagged with both green and yellow/red reporters.

In micrograph (b), the sample is excited with blue light ($\lambda$=450-480 nm) and emission wavelengths below $\lambda$=515 nm are filtered out so that only wavelengths above $\lambda$=515 nm are observed.

The predominantly green carriers in (b) are those which have been tagged with fluorescent green reporters in Procedure A in Example 3. Of these predominantly green carriers, there are two different species of carrier; those exhibiting both green and yellow reporters and those exhibiting only green reporters. The former carriers are those that have been tagged with green and yellow/red reporters. The latter carriers are those that have been tagged with green and blue reporters but the blue reporters cannot be observed under this excitation.

The predominantly yellow carriers in (b) are those which have been tagged with fluorescent green reporters in Procedure A in Example 3. Of these predominantly yellow carriers, there are two different species of carrier; those exhibiting both red and yellow reporters and those exhibiting only red reporters. The former carriers are those that have been tagged with green and yellow/red reporters. The latter carriers are those that have been tagged with red and blue reporters but the blue reporters cannot be observed under this excitation.

In the lower micrograph (c), the sample is excited with green light ($\lambda$=510-550 nm) and emission wavelengths below $\lambda$=590 nm are filtered out so that only wavelengths above $\lambda$=590 nm are observed.

The dark carriers in (c) are those which have been tagged with fluorescent green reporters in Procedure A in Example 3 and fluorescent blue reporters in Procedure E in Example 3. The fluorescent green and the fluorescent blue reporters cannot be observed under this excitation, and so the carriers which have been tagged with green and blue, appear dark.

The red carriers in (c) are those which have been tagged with fluorescent red reporters in Procedure A in Example 3 and fluorescent yellow/red or blue reporters in Procedure E in Example 3. Those carriers which were tagged with both red and yellow/red reporters can be distinguished from those which were tagged with both red and blue by referring to micrograph (b).

The darker (less red) carriers in (b) are those which have tagged with fluorescent green reporters in Procedure A in Example 3 and fluorescent yellow/red reporters in Procedure E in Example 3. The fluorescent green reporters cannot be observed under this excitation but the red signal form the combined yellow/red reporters can be observed.

Thus, the red carriers in (c) are predominantly yellow in (b) and red/pink in (a), and the dark carriers in (c) are predominantly green in (b) and green/aqua in (a).

Example 4

Verification of Coding by Mass Spectrometry

Procedure A:

FMOC-L-Glu-p-benzyloxybenzal alcohol resin (WANG resin) (100 mg, 0.61 mmol/g, Auspep) is deprotected by shaking with excess (10 ml) piperidine/DMF (1:1) for 2 minutes. The solvent is removed by vacuum filtration. Fresh piperidine/DMF is added and the resin is shaken for a further 2 minutes. The solvent is removed and the resin is washed with DMF (5×20 ml) and DCM/Methanol (1:1) and dried under nitrogen gas.

Procedure B:

The resin is added to 0.25 ml of red polyelectrolyte coated silica reporters. Refer to Example I for preparation of polyelectrolyte coated silica reporters. The resin is washed with excess DMF (20×20 ml). The solvent and free reporters are removed by vacuum filtration through a glass sinter of pore size 1740 μm. After the final wash, the resin remains in DMF.

Procedure C:

The monomer Fmoc-Glycine-OH (150 mg, 0.5 mmol, Novabiochem) is mixed with N-[1H-(benzotriazol-1-yl)(dimethylamino)methylene]-N-methylmethanaminimum hexafluorophosphate N-oxide (HBTU, 0.5 mmol, 0.5 M, 1 ml) and diisopropylethylamine (DIEA, 0.6 mmol, 120 μl). The activated amino acid is added to the red-tagged beads (100 mg) as prepared in Procedure B and shaken for 10 minutes. The resin is washed with DMF (5×20 ml).

Procedure D:

The resin is deprotected by shaking with excess (10 ml) piperidine/DMF (1:1) for 2 minutes. The solvent is removed by vacuum filtration. Fresh piperidine/DMF is added and the resin is shaken for a further 2 minutes. The piperidine is removed by washing with DMF (5×20 ml).

Procedure E:

The resin is added to 0.25 ml of green polyelectrolyte coated silica reporters. Refer to Example 1 for preparation of polyelectrolyte coated silica reporters. The resin is washed with excess DMF (20×20 ml). The solvent and free reporters are removed by vacuum filtration through a glass sinter of pore size 17-40 μm. After the final wash, the resin remains in DMF.

Procedure F:

The monomer Fmoc-Lysine(Boc)-OH (235 mg, 0.5 mmol, Novabiochem) is mixed with HBTU (0.5 mmol, 0.5 M, 1 ml) and diisopropylethylamine (DIEA, 0.6 mmol, 120 μl). The activated amino acid is added to the resin (100 mg) as prepared in Procedure E and shaken for 10 minutes. The resin is washed with DMF (5×20 ml).

Procedure G:

The resin is deprotected by shaking with excess (10 ml) piperidine/DMF (1:1) for 2 minutes. The solvent is removed by vacuum filtration. Fresh piperidine/DMF is added and the resin is shaken for a further 2 minutes. The piperidine is removed by washing with DMF (5×20 ml).

Procedure H:

The resin is added to 0.25 ml of blue polyelectrolyte coated silica reporters. The resin is washed with excess DMF (20×20 ml). The solvent and free reporters are removed by vacuum filtration through a glass sinter of pore size 17-40 μm. After the final wash, the resin remains in DMF.

Procedure I:

The monomer Fmoc-Alanine-OH (160 mg, 0.5 mmol, Novabiochem) is mixed with HBTU (0.5 mmol, 0.5 M, 1 ml) and diisopropylethylamine (DIEA, 0.6 mmol, 120 μl). The activated amino acid is added to the resin (100 mg) as prepared in Procedure E and shaken for 10 minutes. The resin is washed with DMF (5×20 ml) and DCM/methanol (1:1) (5×20 ml) and dried under nitrogen gas.

Procedure J:

In order to check the nature of the peptide which was synthesized and tagged in the abovementioned Procedures, the peptide was cleaved from the resin and examined by mass spectroscopy. The sample for mass spectroscopy was prepared in the following way:

Five mg of the dried resin from Procedure I was added to a solution of 95% TFA in water (300 ml) and left for one hour. The solution was removed by passing nitrogen gas over the resin. When dry, a 50% acetonitrile in water solution (pH=2, 100 μl) was added to the resin and 10 μl of this solution was used for mass spectroscopy analysis. The mass spectrum is shown in FIG. 16. The largest peak is at 626.1 which corresponds to the molecular weight of Fmoc-Alanine-Glycine-Lysine-Glycine-OH (SEQ ID NO:1). This is the exact peptide sequence which was synthesized on the carriers in this three-step amino acid coupling and tagging example.

Example 5

It will be appreciated that Examples 1-4 may be repeated with reporter beads having any number of different surface coatings attached to different types of carrier beads. The resulting combination of carrier bead and attached reporter beads is stable in DMF. In this example, it was found that reporter beads selected from the group consisting of silica beads functionalized with —COOH, silica beads functionalized with PEI, silica beads functionalized with PEI and polyacrylic acid, silica beads functionalized with —NH$_2$, uncoated silica beads and polystyrene/DVB beads functionalized with sulfate groups were attached to carrier beads selected from Boc and Fmoc protected resins, aminomethylated resin, polystyrene/polyethylene glycol (TENTAGEL) SOH resin, MBHA resin and protected 4-hydroxymethylphenylacetamidomethyl (PAM) resin.

Example 6

Variations to Attachment Procedures

The number of reporter beads per carrier can be manipulated and relies to some extent on the reporter concentration before carriers are added, reporter bead size, functional groups on the reporter bead and carrier surfaces, and is to a certain extent, time-dependent. Polyelectrolyte coating of the reporters may be used if desired to improve the reporter bead adhesion.

Successful attachment can be achieved by several procedures as described hereinafter.

Procedure A:

Dry carrier beads can be added to a concentrated solution of reporters in solvent as exemplified by the following:—

Aminomethylated resin (100 mg, 0.26 mmol/g, Peptide Institute) is added to 0.25 ml of red polyelectrolyte-coated silica reporters (10 mg/ml) in DMF, prepared as per Example 1.

Procedure B:

Carrier beads are swelled in excess solvent and added to a concentrated solution of reporters in solvent as exemplified by the following:—

Aminomethylated resin (100 mg, 0.26 mmol/g, Peptide Institute) is swelled in DMF and added to 1 ml of red polyelectrolyte-coated silica reporters (10 mg/ml) in DMF, prepared as per Example 1.

Procedure C:

Deprotection and tagging is performed in one step, by mixing the reporter-DMF suspension (as prepared in Example 1) with an equal volume of piperidine and adding to swelled Fmoc-protected carrier beads as shown by the following:—

A. 1 ml suspension of fluorescent red polyelectrolyte-coated reporters in DMF (10 mg/ml, as prepared in Example 1) is shaken with Fmoc-Glycine-resin (100 mg) and 1 ml piperidine for 5 minutes. The solvent is removed and a fresh solution of reporters in piperidine/DMF is shaken with the carriers for another 5 minutes.

Example 7

Washing Procedures

Free reporter beads can be removed from the solvent by vacuum filtration through a glass sinter of pore size 17-40 μl (refer to Procedure B in Example 1) or by other methods such as centrifugation or through the use of magnetic carrier or reporter beads.

Example 8

Effect of Various Organic Solvents and Reaction Conditions on Reporter Bead Adhesion and Exchange Procedure A:

Examination of reporter exchange in dichloromethane in the presence of excess $Pd(PPh_3)_4$ and diethylazodicarboxylate (DEAD).

Red-tagged carriers (100 mg) and green-tagged carriers (100 mg) are prepared and washed as per Procedure B in Example 3. The red-tagged and the green-tagged carriers are mixed together in DMF and subsequently washed with DCM/methanol then dried under nitrogen gas. 10 mg of the dry carriers is placed into DCM (0.3 ml) with $Pd(PPh_3)_4$ and diethylazodicarboxylate (DEAD). No detectable exchange between red-tagged and green-tagged carriers is observed over a 24 hour period.

Procedure B

The reporter-carrier bead adhesion also survives the following conditions, with no apparent detachment of reporters from the carrier beads and no significant amount of reporter exchange between carriers:—

(i) Red-tagged and green-tagged carrier beads together in organic solvents selected from DMF, THF, DCM, acetonitrile, ethylacetate and methanol.

(ii) Red-tagged and green-tagged resin beads together in organic solvents selected from DMF, THF, acetonitrile, ethylacetate and methanol and heated to 50° C. for 45 minutes.

(iii) Red-tagged and green-tagged resin beads together in organic solvents selected from DMF and diisopropyl ethylamine (DIEA), THF-NaH (some resin beads break up within 2 hours, most still intact with reporters after 20 hrs), and methanol-$NaOCH_3$ in the presence of base;

(iv) Red-tagged and green-tagged resin beads together in organic solvents selected from DMF and diisopropyl ethylamine (DIEA) and methanol-$NaOCH_3$ in the presence of base and heated to 50° C. for 45 minutes;

(v) Red-tagged and green-tagged resin beads together in organic solvents selected from DCM-TFA (4:1) and DCM-acetic acid in the presence of acid;

(vi) Red-tagged and green-tagged resin beads together in organic solvents comprising methanol containing sodium cyanoborohydride and DCM containing $Pd(PPh_3)_4$;

(vii) Red-tagged and green-tagged resin beads together in organic solvents with reducing agents selected from DCM-pyridine dichromate (resin tends to break up, but reporters are still attached), DMF-5-nitro-2-hydroxy benzaldehyde and DCM-$Pd(PPh_3)_4$-diethylazo-dicarboxylate (DEAD); and (viii) Red-tagged and green-tagged resin beads together in DMF with peptide coupling reagents comprising FMOC-Gly-OH, HBTU and DIEA.

Procedure C:

Procedure A of Example 3 was repeated with the exception that DMF was replaced by various solvents selected from water, methanol, DCM, acetic acid, water/DMF (4:1) piperidine/DMF (1:1) and methanol/DCM (1:1). Similar results were obtained.

Example 9

Gamma Irradiation of Polyelectrolyte Coated Reporter Beads

In this Example, the polyelectrolyte coated reporter beads were prepared by allowing PEI, then PAA, to adsorb onto the silica beads. These reporter beads showed excellent attachment to various types of carriers. The attachment could be further improved by creation of a larger mesh on the surface of the reporter. This can be achieved by γ-irradiation of the polyelectrolyte coated reporters in a polyelectrolyte solution during the coating procedure. Formation of radicals along the polyelectrolyte chains under gamma irradiation allows cross-linking to occur. This creates a large mesh around the reporter, which enhances the strength of attachment to the carriers by allowing better bridging flocculation. This is exemplified by the following procedure:—

Fluorescent red silica microspheres (10 mg, 1 μm diameter, Microcaps, GmbH) are added to an aqueous solution of PEI (3 ml, 1.2% by weight, MWt. 10000 g/mol, Polysciences Inc.) and sonicated for 30 minutes. The reporter solution is equilibrated for 24 hours to allow adsorption of PEI onto the reporters. The reporters are washed in RO water (MILLI-Q) to remove PEI (5×3 ml) and are resuspended in an aqueous solution of PAA (3 ml, 0.75%, M. Wt.=250000 g/mol, Sigma-Aldrich). Nitrogen gas is bubbled through the solution for 30 minutes to remove oxygen which can act as a scavenger for the radicals formed under gamma irradiation. The solution is then placed in the gamma cell for 1.5 hours at a dose rate of 8 kG/hour (i.e., total dose 11.5-12 kG). The reporters are washed in RO water (MILLI-Q) (5×3 ml) and DMF (5×3 ml) and are left in 1 ml DMF (final reporter concentration=10 mg/ml).

Example 11

Dendrimers

The presence of a mesh of dendritic macromolecules on a carrier bead, reporter bead, or both may enhance the permanent attachment of reporter beads to the carrier. Dendritic macromolecules (dendrimers) are a new class of material (Tsukruk et al., 1997, Langmuir 13 2171) and have a cascade, branched architecture. Manipulation of the macromolecule properties of dendrimers can be achieved by systematic structural variation of the "core" and "branching units" (monomers). The surface porosity, the size and location of specific cavities in the dendritic structure and the final shape of the dendrimer will be affected by these variations.

Example of Tagging Dendrimers with Reporters

Polyamidoamine dendrimers in DMF (0.25 ml, 200 mg/ml, Generation 10, Dendritech) are mixed with red reporters (1 μm diameter, 0.25 ml, 10 mg/ml, Microcaps GmbH) which have been coated with polyelectrolyte (refer to Example 2). After tagging, free reporters are removed by washing with DMF (20×20 ml) and vacuum filtration through a glass sinter.

```
                              SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Synthetically generated peptide
<221> NAME/KEY: VARIANT
<222> LOCATION: 1
<223> OTHER INFORMATION: Xaa = 9-fluorenylmethoxycarbonyl (Fmoc)
<221> NAME/KEY: VARIANT
<222> LOCATION: 6
<223> OTHER INFORMATION: Xaa = hydroxy group (OH)

<400> SEQUENCE: 1

Xaa Ala Gly Lys Gly Xaa
 1               5
```

Example 10

Covalent Bonding to Reinforce Reporter-Carrier Attachment

Once reporter bead attachment to carriers has been induced through manipulation of colloidal forces, the robustness of attachment may be strengthened through the formation of supplementary covalent bonds between surface groups of the two colloids. For example, a peptide bond can be formed between deprotected $NH_2$ on the surface of a carrier and COOH groups on the surface of the reporters (in the presence of coupling agent HBTU and base DIEA). Alternatively, a similar covalent reaction can be induced after attachment of particles by bridging floculation. For example, the reporters may be coated with PAA mesh, floculated and reacted to a carrier bead containing $NH_2$-surface groups.

The invention claimed is:

1. A composition comprising a colloidal carrier particle having a plurality of distinguishable colloidal reporter particles non-covalently coagulated thereto, wherein each colloidal reporter particle comprises a marker, and wherein said carrier particle is suitable for use in solid phase synthesis and is suitable for covalent attachment of at least one chemical group.

2. A composition as claimed in claim 1 wherein the marker is selected from the group consisting of a fluorophore, a chromophore, a bar code, a radioactive label, a luminescent label and a detectable physical feature of the particle.

3. A composition as claimed in claim 1 wherein the colloidal carrier particle is a polymeric bead having a diameter of 1 to 1000 μm.

4. A composition as claimed in claim 1 wherein the colloidal carrier particle comprises a material selected from the group consisting of a bead formed from polystyrene crosslinked with 1-5% divinylbenzene, hexamethylenediamine-polyacryl resin, poly[N-{2-(4-hydroxylphenyl) ethyl}] acrylamide, silica, cellulose, polystyrene, latex, grafted copolymers, polyethylene glycol/polystyrene, poreglass, polyacrylamide, dimethylacrylamide optionally cross-linked with N,N'-bis-acrylolyl ethylene diamine, glass particles coated with a hydrophobic polymer cross-linked polystyrene, a fluorinated ethylene polymer, poly(N-acryloylpyrrolidine) resin, p-benzyloxyl benzyl alcohol resin (WANG resin), 4-hydromethylphenylacetamidomethyl resin (PAM resin), chloromethylpolystyrene-divinylbenzene resin (MERRIFIELD resin), polyethylene glycol/polystyrene resin (PAP resin), polyamide resin, polyethylene functionalized with acrylic acid, kieselguhr/polyamide (Pepsyn K), polyacrylamide/polystyrene copolymer (POLYHIPE), polystyrene/polydimethylacrylamide copolymers, controlled pore glass (CPG), polystyrene macrobeads, polystyrene/polyethylene glycol (TENTAGEL) and polyethylene glycol-polystyrene/divinylbenzene copolymers.

5. A composition as claimed in claim 1 wherein the colloidal carrier particle contains functionalities selected from the group consisting of —NH$_2$, —COOH, —SOH, —SSH and sulfate.

6. A composition as claimed in claim 1 wherein the carrier particle comprises a form selected from the group consisting of a bead, a pellet, a disc, a capillary, a hollow fibre needle, a pin and a chip.

7. A composition as claimed in claim 1 wherein each colloidal reporter particle is a ceramic microparticle having a diameter of about 0.1 μm to 50 μm.

8. A composition as claimed in claim 7 wherein the ceramic microparticle is a silica microparticle.

9. The composition according to claim 1, wherein said colloidal reporter particles comprise a polyelectrolytic coating.

10. The composition according to claim 1, wherein a linker is covalently attached to said carrier particle.

11. The composition according to claim 1, wherein a chemical group is covalently attached to said carrier particle.

12. The composition according to claim 1, wherein said reporter particles are smaller than said carrier particle.

13. The composition according to claim 12, wherein each marker is a fluorophore, and wherein a plurality of said reporter particles comprise distinguishable fluorophores.

* * * * *